(12) United States Patent
Vetter et al.

(10) Patent No.: US 7,044,956 B2
(45) Date of Patent: May 16, 2006

(54) METHODS AND DEVICES FOR CUTTING AND COLLECTING SOFT TISSUE

(75) Inventors: James W. Vetter, Portola Valley, CA (US); Ary S. Chernomorsky, Walnut Creek, CA (US); Mark J. Clifford, Los Altos, CA (US); Dan Brounstein, Fremont, CA (US); Scott C. Anderson, Sunnyvale, CA (US)

(73) Assignee: Rubicor Medical, Inc., Redwood City, CA (US)

( * ) Notice: Subject to any disclaimer, the term of this patent is extended or adjusted under 35 U.S.C. 154(b) by 0 days.

(21) Appl. No.: 10/272,452

(22) Filed: Oct. 16, 2002

(65) Prior Publication Data

US 2004/0006338 A1     Jan. 8, 2004

Related U.S. Application Data

(63) Continuation-in-part of application No. 10/189,277, filed on Jul. 3, 2002.

(51) Int. Cl.
*A61B 17/32*    (2006.01)
(52) U.S. Cl. .................................... 606/167
(58) Field of Classification Search ........ 606/159–180; 600/564–567, 568; 128/898
See application file for complete search history.

(56) References Cited

U.S. PATENT DOCUMENTS

| | | |
|---|---|---|
| 1,813,902 A | 7/1931 | Bovie |
| 2,816,552 A | 12/1957 | Hoffman |
| 3,320,957 A | 5/1967 | Sokolik |
| 3,732,858 A | 5/1973 | Banko |
| 3,749,085 A | 7/1973 | Wilson |
| 3,910,279 A | 10/1975 | Okada |
| 3,955,578 A | 5/1976 | Chamness et al. |
| 4,099,518 A | 7/1978 | Baylis et al. |
| 4,245,653 A | 1/1981 | Weaver |
| 4,347,846 A | 9/1982 | Dormia |
| 4,611,594 A | 9/1986 | Grayhack |
| 4,650,466 A | 3/1987 | Luther |
| 4,890,611 A | 1/1990 | Monfort |
| 4,903,696 A | 2/1990 | Stasz |
| 4,966,604 A | 10/1990 | Reiss |
| 5,071,424 A | 12/1991 | Reger |
| 5,083,570 A | 1/1992 | Mosby |

(Continued)

FOREIGN PATENT DOCUMENTS

DE         195 28 440 A1     2/1997

(Continued)

OTHER PUBLICATIONS

International Search Report mailed May 12, 2005, in corresponding international Application No. PCT/US03/20364.

*Primary Examiner*—Vy Q. Bui
(74) *Attorney, Agent, or Firm*—Young Law Firm, P.C.

(57) ABSTRACT

Devices and methods for cutting and collecting a specimen from a mass of tissue. The device may include an integrated cut and collect assembly. The integrated cut and collect assembly includes a cutting portion and a collection portion that includes a flexible membrane. The collection portion of the assembly is attached to the cutting portion thereof. The cutting portion is configured to cut the specimen from the mass of tissue and the collection portion is configured to collect the cut specimen and to encapsulate and isolate the cut specimen within the membrane to enable its safe retraction from the mass of tissue.

22 Claims, 11 Drawing Sheets

U.S. PATENT DOCUMENTS

| | | |
|---|---|---|
| 5,100,423 A | 3/1992 | Fearnot |
| 5,147,355 A | 9/1992 | Friedman et al. |
| 5,152,293 A | 10/1992 | Vonesh |
| 5,156,610 A | 10/1992 | Reger |
| 5,174,296 A | 12/1992 | Watanabe |
| 5,176,688 A | 1/1993 | Narayan |
| 5,192,291 A | 3/1993 | Pannek, Jr. |
| 5,211,651 A | 5/1993 | Reger |
| 5,217,479 A | 6/1993 | Shuler |
| 5,224,488 A | 7/1993 | Neuffer |
| 5,224,945 A | 7/1993 | Pannek, Jr. |
| 5,282,484 A | 2/1994 | Reger |
| 5,308,321 A | 5/1994 | Castro |
| 5,318,576 A | 6/1994 | Plassche, Jr. |
| 5,325,860 A | 7/1994 | Seward |
| 5,415,656 A | 5/1995 | Tihon et al. |
| 5,441,510 A | 8/1995 | Simpson |
| 5,527,326 A | 6/1996 | Hermann |
| 5,554,163 A | 9/1996 | Shturman |
| 5,630,426 A | 5/1997 | Eggers |
| 5,632,754 A | 5/1997 | Farley |
| 5,672,172 A | 9/1997 | Zupkas |
| 5,709,697 A | 1/1998 | Ratcliff |
| 5,766,191 A | 6/1998 | Trerotola |
| 5,794,626 A | 8/1998 | Kieturakis |
| 5,895,399 A | 4/1999 | Barbut |
| 5,913,855 A | 6/1999 | Gough et al. |
| 5,928,159 A | 7/1999 | Eggers |
| 5,928,164 A | 7/1999 | Burbank |
| 5,947,964 A | 9/1999 | Eggers |
| 5,954,655 A | 9/1999 | Hussman |
| 5,954,670 A | 9/1999 | Baker |
| 6,015,390 A | 1/2000 | Krag |
| 6,022,362 A | 2/2000 | Lee |
| 6,036,708 A | 3/2000 | Sciver |
| 6,063,082 A | 5/2000 | DeVore |
| 6,080,149 A | 6/2000 | Huang |
| 6,080,151 A | 6/2000 | Swartz et al. |
| 6,096,053 A | 8/2000 | Bates |
| 6,099,534 A | 8/2000 | Bates |
| 6,106,524 A | 8/2000 | Eggers |
| 6,179,860 B1 | 1/2001 | Fulton, III |
| 6,221,006 B1 | 4/2001 | Dubrul |
| 6,238,389 B1 | 5/2001 | Paddock et al. |
| 6,280,450 B1 | 8/2001 | McGuckin, Jr. |
| 6,325,797 B1 | 12/2001 | Stewart et al. |
| 6,331,166 B1 | 12/2001 | Burbank |
| 6,387,056 B1 | 5/2002 | Kieturakis |
| 6,471,709 B1 * | 10/2002 | Fawzi et al. ................ 606/114 |
| 6,514,248 B1 | 2/2003 | Eggers et al. |
| 6,602,204 B1 | 8/2003 | Dubrul et al. |
| 6,605,047 B1 | 8/2003 | Zarins et al. |
| 2001/0047169 A1 | 11/2001 | McGuckin, Jr. |
| 2002/0058885 A1 | 5/2002 | Burbank et al. |

FOREIGN PATENT DOCUMENTS

| | | |
|---|---|---|
| DE | 197 06 751 A1 | 2/1997 |
| DE | 19706751 A1 | 10/1997 |
| EP | 0 472 368 B1 | 2/1992 |
| EP | 0 829 232 A3 | 3/1998 |
| EP | 0 908 156 A1 | 11/2003 |
| FR | 2275226 | 5/1975 |
| GB | 1 331 468 | 9/1973 |
| GB | 2 204 496 A | 11/1988 |
| GB | 2204496 | 9/1991 |
| GB | 2311468 A | 1/1997 |
| GB | 2311468 | 10/1997 |
| JP | 61 029 733 | 2/1986 |
| NL | 1004723 | 9/1912 |
| SU | 1235497 | 6/1986 |
| SU | 1355266 | 11/1987 |
| WO | WO 92/20291 | 11/1992 |
| WO | WO 95/02370 | 1/1995 |
| WO | WO 95/02371 | 1/1995 |
| WO | WO 96/29946 | 10/1996 |
| WO | WO 98/08441 | 3/1998 |
| WO | WO 99/01074 | 1/1999 |
| WO | WO 99/04704 | 2/1999 |
| WO | WO 99/43262 | 9/1999 |
| WO | WO 99/44506 | 9/1999 |
| WO | WO 99/44506 | 10/1999 |
| WO | WO 99/53851 | 10/1999 |
| WO | WO 00/10471 | 3/2000 |
| WO | WO 00/12009 | 3/2000 |
| WO | WO 00/16697 | 3/2000 |
| WO | WO 00/30531 | 6/2000 |
| WO | WO 00/33743 | 6/2000 |
| WO | WO 00/12009 | 8/2000 |
| WO | WO 00/16697 | 8/2000 |
| WO | WO 00/44295 | 8/2000 |
| WO | WO 00/45854 | 8/2000 |
| WO | WO 00/10471 | 11/2000 |
| WO | WO 00/74561 A1 | 12/2000 |
| WO | WO 01/28445 A1 | 4/2001 |
| WO | WO 01/28446 A1 | 4/2001 |

* cited by examiner

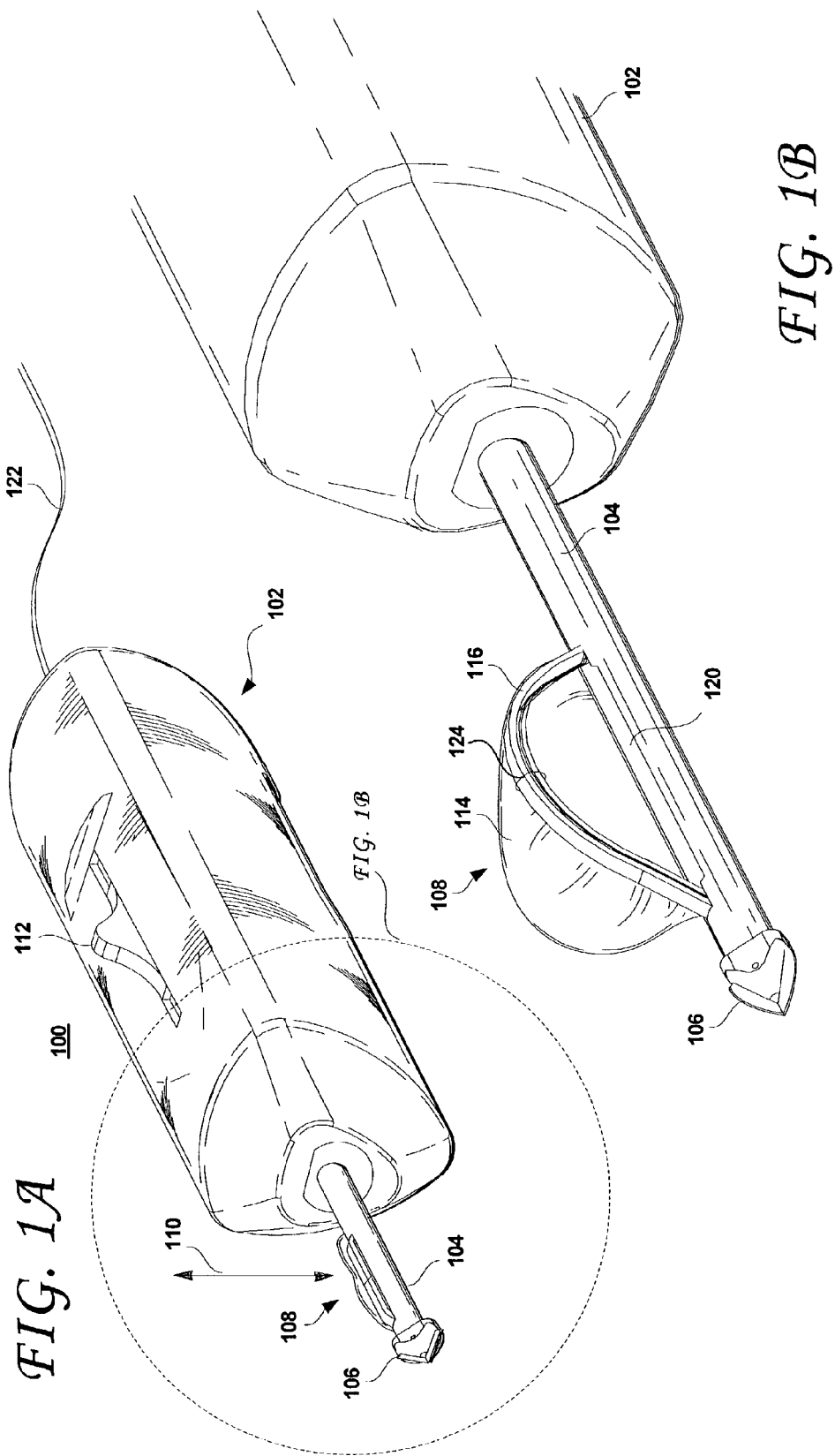

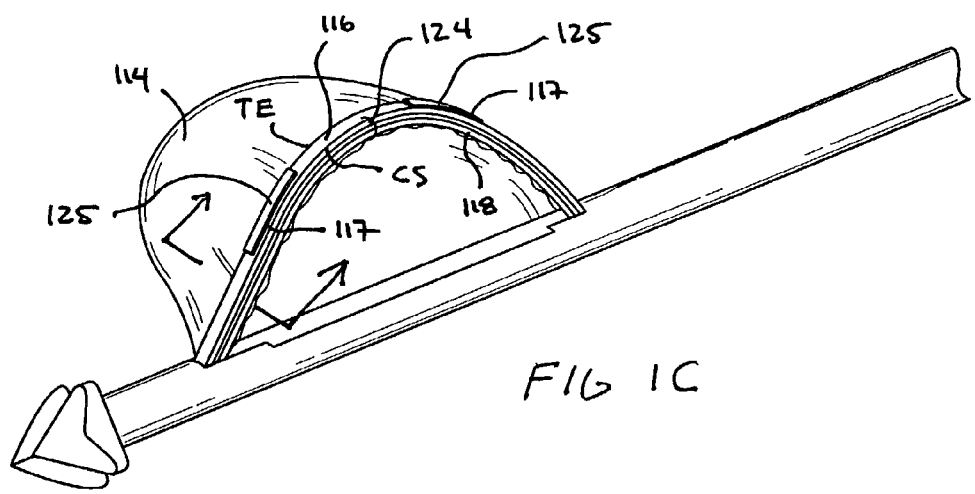
FIG 1C
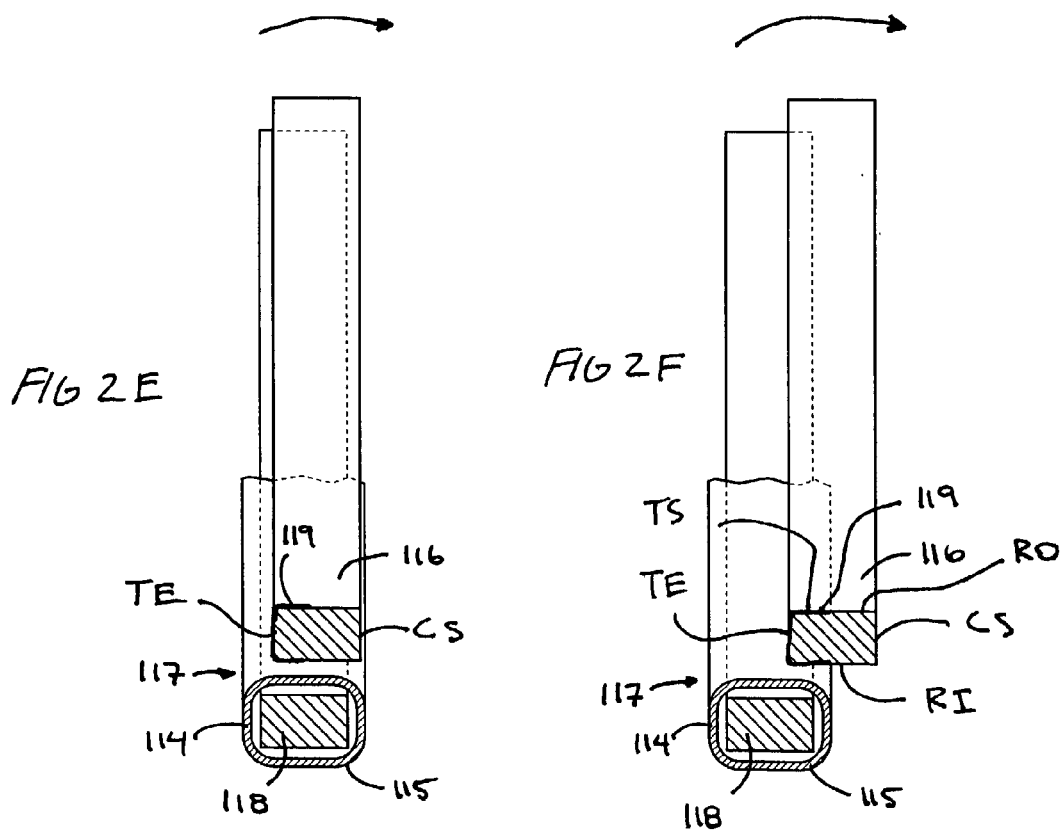
FIG 2E
FIG 2F

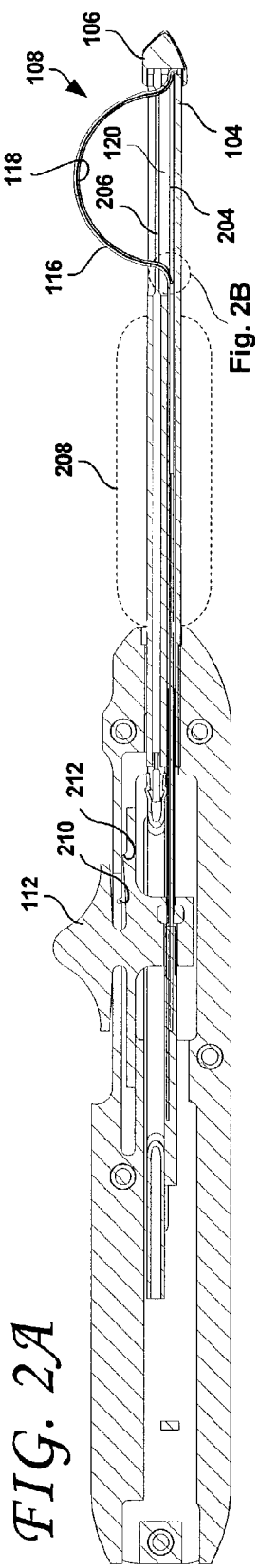
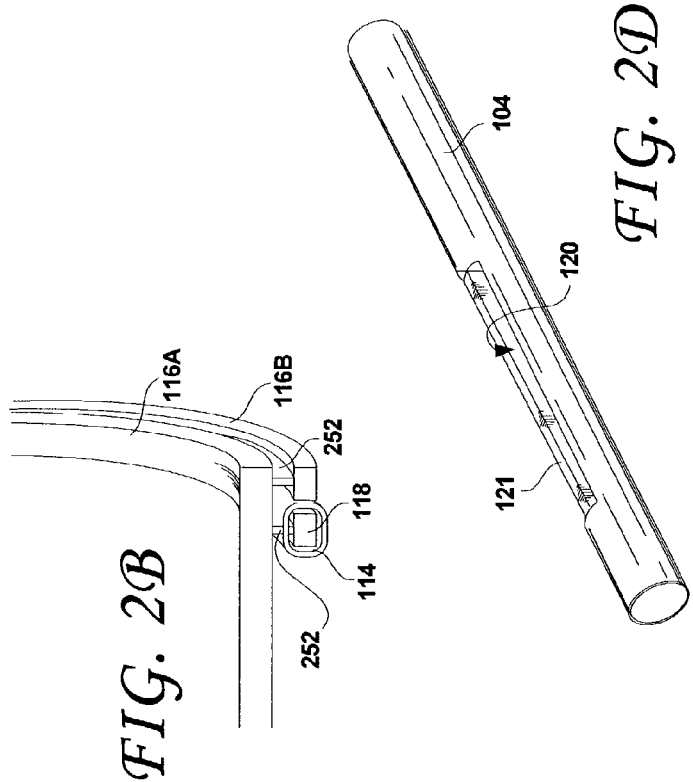
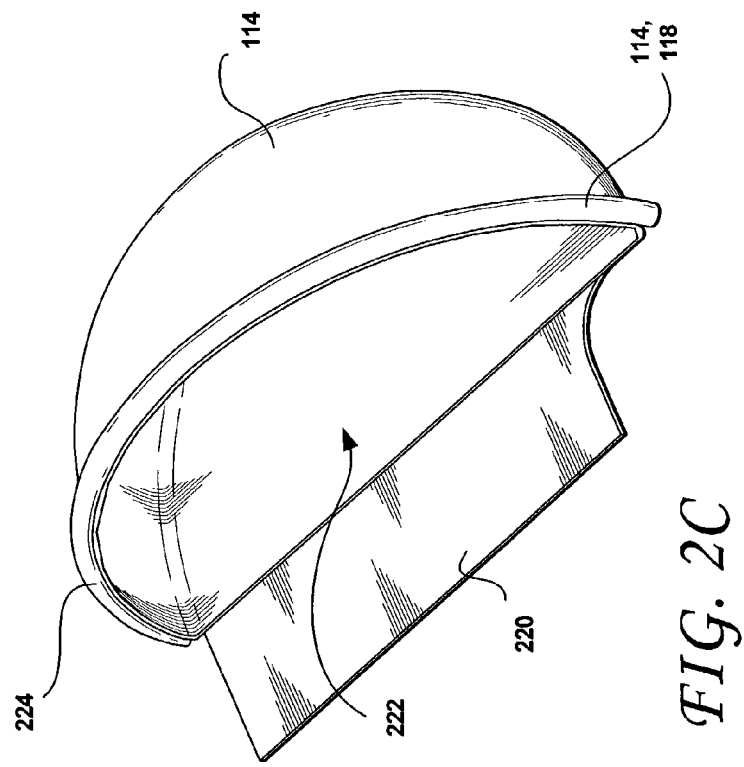

METHODS AND DEVICES FOR CUTTING AND COLLECTING SOFT TISSUE

This application is a continuation in part of commonly assigned and copending U.S. patent application Ser. No. RUBI5801 10/189,277 filed on Jul. 3, 2002, which is hereby incorporated by reference.

BACKGROUND OF THE INVENTION

1. Field of the Invention

The present invention pertains to the field of soft tissue excisional devices and methods. In particular, the present invention relates to the field of devices and methods for excising specimen from soft tissue, such as breast tissue, for example.

2. Description of the Related Art

Breast cancer is a major threat and concern to women. Early detection and treatment of suspicious or cancerous lesions in the breast has been shown to improve long-term survival of the patient. The trend is, therefore, to encourage women not only to perform monthly self-breast examination and obtain a yearly breast examination by a qualified physician, but also to undergo annual screening mammography commencing at age 40. Mammography is the only screening modality available today that can detect small, nonpalpable lesions. These nonpalpable lesions may appear as opaque densities relative to normal breast parenchyma and fat or as clusters of microcalcifications.

The conventional method for diagnosing, localizing and excising nonpalpable lesions detected by mammography generally involves a time-consuming, multi-step process. First, the patient goes to the radiology department where the radiologist finds and localizes the lesion either using mammography or ultrasound guidance. Once localized, a radio-opaque wire is inserted into the breast. The distal end of the wire may include a small hook or loop. Ideally, this is placed adjacent to the suspicious area to be biopsied. The patient is then transported to the operating room. Under general or local anesthesia, the surgeon performs a procedure called a needle-localized breast biopsy. In the needle-localized breast biopsy, the surgeon, guided by the wire previously placed in the patient's breast, excises a mass of tissue around the distal end of the wire. The specimen is sent to the radiology department where a specimen radiograph is taken to confirm that the suspicious lesion is contained within the excised specimen. Meanwhile, the surgeon, patient, anesthesiologist and operating room staff, wait in the operating room for confirmation of that fact from the radiologist before the operation is completed. The suspicious lesion should ideally be excised in toto with a small margin or rim of normal breast tissue on all sides. Obtaining good margins of normal tissue is extremely dependent upon the skill and experience of the surgeon, and often an excessively large amount of normal breast tissue is removed to ensure that the lesion is located within the specimen. This increases the risk of post-operative complications, including bleeding and permanent breast deformity. As 80% of breast biopsies today are benign, many women unnecessarily suffer from permanent scarring and deformity from such benign breast biopsies.

More recently, less invasive techniques have been developed to sample or biopsy the suspicious lesions to obtain a histological diagnosis. The simplest of the newer techniques is to attempt visualization of the lesion by external ultrasound. If seen by external ultrasound, the lesion can be biopsied while being continuously visualized. This technique allows the physician to see the biopsy needle as it actually enters the lesion, thus ensuring that the correct area is sampled. Current sampling systems for use with external ultrasound guidance include a fine needle aspirate, core needle biopsy or vacuum-assisted biopsy devices.

Another conventional technique localizes the suspicious lesion using stereotactic digital mammography. The patient is placed prone on a special table that includes a hole to allow the designated breast to dangle therethrough. The breast is compressed between two mammography plates, which stabilizes the breast to be biopsied and allows the digital mammograms to be taken. At least two images are taken at two angular positions to obtain stereotactic views. The x, y and z coordinates targeting the lesion are calculated by a computer. The physician then aligns a special mechanical stage mounted under the table that places the biopsy device into the breast to obtain the sample or samples. There are believed to be three methods available to biopsy lesions using a stereotactic table: (1) fine needle aspiration, (2) core needle biopsy and (3) vacuum-assisted core needle biopsy.

Fine needle aspiration uses a small gauge needle, usually 20 to 25 gauge, to aspirate a small sample of cells from the lesion or suspicious area. The sample is smeared onto slides that are stained and examined by a cytopathologist. In this technique, individual cells in the smears are examined, and tissue architecture or histology is generally not preserved. Fine needle aspiration is also very dependent upon the skill and experience of the operator and can result in a high non-diagnostic rate (up to about 83%), due to inadequate sample collection or preparation.

Core needle biopsy uses a larger size needle, usually 14 gauge to sample the lesion. Tissue architecture and histology are preserved with this method. A side-cutting device, consisting of an inner trough with an outer cutting cannula is attached to a spring-loaded device for a rapid semi-automated firing action. After the lesion is localized, local anesthetic is instilled and a small incision is made in the skin with a scalpel. The device enters the breast and the needle tip is guided into the breast up to the targeted lesion. The device is fired. First, the inner cannula containing the trough rapidly penetrates the lesion. Immediately following this, the outer cutting cannula rapidly advances over the inner cannula cutting a sample of tissue off in the trough. The whole device is then removed and the sample retrieved. Multiple penetrations of the core needle through the breast and into the lesion are required to obtain an adequate sampling of the lesion. Over 10 samples have been recommended by some.

The vacuum-assisted breast biopsy system is a larger semi-automated side-cutting device. It is usually 11 gauge in diameter and is more sophisticated than the core needle biopsy device. Multiple large samples can be obtained from the lesion without having to reinsert the needle each time. A vacuum is added to suck the tissue into the trough. The rapid firing action of the spring-loaded core needle device is replaced with an oscillating outer cannula that cuts the breast tissue off in the trough. The physician controls the speed at which the outer cannula advances over the trough and can rotate the alignment of the trough in a clockwise fashion to obtain multiple samples.

If a fine needle aspirate, needle core biopsy or vacuum-assisted biopsy shows malignancy or a specific benign diagnosis of atypical hyperplasia, then the patient needs to undergo another procedure, the traditional needle-localized breast biopsy, to fully excise the area with an adequate margin of normal breast tissue. Sometimes the vacuum-assisted device removes the whole targeted lesion. If this occurs, a small titanium clip should be placed in the biopsy field. This clip marks the area if a needle-localized breast biopsy is subsequently required for the previously mentioned reasons.

Another method of biopsying the suspicious lesion utilizes a large end-cutting core device measuring 0.5 cm to 2.0 cm in diameter. This also uses the stereotactic table for stabilization and localization. After the lesion coordinates are calculated and local anesthesia instilled, an incision large enough is permit entry of the bore is made at the entry site with a scalpel. The breast tissue is cored down to and past the lesion. Once the specimen is retrieved, the patient is turned onto her back and the surgeon cauterizes bleeding vessels under direct vision. The incision, measuring 0.5 to larger than 2.0 cm is sutured closed.

The stereotactic table requires awkward positioning of the patient and may be extremely uncomfortable. The woman must lie prone during the entire procedure, which may be impossible for some patients. In addition, the lesion to be biopsied must be in the center working area of the mammography plates. This may be extremely difficult and uncomfortable for the patient if the lesion is very posterior near the chest wall or high towards the axilla.

The woman is subjected to increased radiation exposure as multiple radiographs are required throughout the course of the procedure to: (1) confirm that the lesion is within the working area of the mammography plates, (2) obtain the stereotactic coordinates (at least two views), (3) verify the positioning of the biopsy needle prior to obtaining tissue, and (4) verify that the lesion was indeed sampled. If any difficulty is encountered during the procedure, additional radiographic exposures are required to verify correction of the problem.

Using the core needle biopsy or vacuum-assisted device, bleeding is controlled only by manual pressure. Bleeding is generally not an issue with fine needle aspiration, but is a legitimate complication of the former two methods. Ecchymoses, breast edema and hematomas can occur. This causes increased post-procedural pain and delays healing. Rarely, the patient may require an emergency operation to control and evacuate a tense hematoma.

Another major concern is the possibility of tumor dissemination. The core needle biopsy and vacuum-assisted devices both cut into the tumor and carve out multiple samples for examination. While cutting into the tumor, cancerous cells may be dislodged. Cutting across blood vessels at the same time may allow the freed cancerous cells access to the blood stream, thus possibly seeding the tumor beyond its original locus. The long-term consequences of tumor seeding with the risk of blood borne metastases are unknown at this time, as the techniques are relatively new. However, documented instances of cancerous cells seeding locally into needle tracks exist. There are numerous reports of metastases growing in needle tracks from previous biopsies of a cancerous mass. Most of these are from lung or liver cancers. However, at least one case of mucinous carcinoma of the breast growing in a needle track has been reported. The long-term consequences of neoplasm seeding into needle tracks are currently unknown, again because the techniques are relatively new. Some recommend excision of the entire needle track, including the skin entry site, during the definitive surgical procedure for a diagnosed cancer, whether it is a lumpectomy or a mastectomy. Others assume that with a lumpectomy, the post-operative radiation therapy will destroy any displaced cancer cells in the needle track. With the trend towards treating very small cancers only by excision and without a post-excision course of radiation therapy, the risk of cancer cells metastasizing and growing in needle tracks is very real.

The large core cutting device (0.5 cm to 2.0 cm) generally eliminates the risk of needle track seeding as it is designed to excise the lesion intact. A stereotactic table is required with the same inherent awkwardness for the patient, as discussed above. Bleeding is controlled, albeit manually, requiring that the patient wait until the end of the procedure to be turned over. Compression is used to stabilize the breast and localize the lesions. The breast, however, may be torqued and distorted between the compression plates such that when the plates are removed after the biopsy, the large core track left behind may not be straight, but actually tortuous. This can result in permanent breast deformity.

The location of the insertion site into the breast is dictated by the positioning of the breast in the machine and not by the physician. The entry site is usually away from the cosmetically preferred nipple-areolar complex and is usually located on the more exposed areas of the breast. For the fine needle aspirate, core biopsy and vacuum-assisted devices, the incision is usually very small and the scar almost unappreciable. However, in the case of the large core biopsy device (0.5 to 2.0 cm), a large incision is needed. Such a large incision often results in a non-aesthetically placed scar.

The newer conventional minimally invasive breast biopsy devices have improved in some ways the ability to diagnose mammographically detected nonpalpable lesions. These devices give the patient a choice as to how she wants the diagnosis to be made. Moreover, these devices are substantially less expensive than the older traditional needle-localized breast biopsy. They are not, however, the final solution. Due to the above-discussed problems and risks associated with compression, needle-track seeding, blood borne metastases, bleeding, radiation exposure and awkwardness of the stereotactic table, more refined devices and methods are needed to resolve these issues. Also, the conventional biopsy devices do not consider margins in their excisions and if cancer is diagnosed, the patient must undergo a needle-localized breast lumpectomy to ensure that adequate margins are removed around the cancer. Devices and methods, therefore, must address the problem of obtaining adequate margins so that a second procedure is not required. Margins, moreover, cannot be assessed while the breast is being compressed.

Commonly assigned U.S. Pat. No. 6,022,362 discloses a novel approach to soft tissue excisional devices. As disclosed therein, the excisional device includes independently actuable cutting and collection tools. As shown therein, the device may include a cutting tool attached near the distal tip of the device. At least a distal portion of the cutting tool is configured to selectively bow out of the window and to retract within the window. One embodiment of the device described in this patent also includes an independently actuable tissue collection device that is separate from the cutting device and that is also externally attached near the distal end of the device. In this configuration, the tissue collection device independently collects the tissue severed by the cutting tool as the excisional is rotated and the cutting tool is independently bowed.

SUMMARY OF THE INVENTION

The present invention, according to one embodiment thereof, is a method of cutting breast tissue using RF energy, including the steps of providing a device having an elongate RF cutting element, the elongate RF cutting element having a cutting side, the elongate cutting element being movable between a bowed position and a straightened position; introducing the device into a patient's breast with the RF cutting element in the straightened position; activating the RF cutting element; moving the RF cutting element to the bowed position; retracting tissue away from the RF cutting element while the RF element may be in the bowed position; and rotating the device to cut a portion of breast tissue with the cutting side of the RF cutting element.

The retracting step may be carried out with the device having a thickened portion that trails the cutting side, the thickened portion retracting tissue away from the cutting element. The retracting step may be carried out with the thickened portion being at least two times larger than a cutting element thickness. The retracting step may be carried out with the thickened portion being at least three times larger than a cutting element thickness. The retracting step may be carried out with the thickened portion being spaced from the cutting side by a distance of less than 0.25 inch. The retracting step may be carried out with the device including a tissue collection element that trails the cutting element. The retracting step may be carried out with the thickened portion retracting tissue away from a radially inner surface of the cutting element when the cutting element is in the bowed position. The retracting step may be carried out with the thickened portion retracting tissue away from a radially outer surface of the RF cutting element. The retracting step may be carried out with the thickened portion retracting tissue away from a radially outer surface of the RF cutting element. The retracting step may be carried out with the thickened portion not transmitting energy for cutting the tissue. The retracting step may be carried out with a side of the cutting element opposite the cutting side being electrically insulated so that RF energy is not delivered to the tissue from the side of the cutting element opposite the cutting side. The retracting step may be carried out with a separate element that is independently movable relative to the cutting element. The retracting step may be carried out with the separate element being movable between bowed and retracted positions. The retracting step may be carried out with the separate element including a tissue collection element that collects tissue cut by the cutting element.

According to another embodiment thereof, the present invention is a device for cutting breast tissue using RF energy, comprising: a shaft; an elongate RF cutting element coupled to the shaft, the elongate RF cutting element having a cutting side, the elongate cutting element being movable between a bowed position and a straightened position; and a tissue retractor that may be also movable between a bowed position and straightened position, the tissue retractor having a thickened portion positioned to retract tissue away from the cutting element when the cutting element and tissue retractor are in the bowed positions.

The shaft may have a longitudinal axis, and rotation of the shaft about the longitudinal axis may move the cutting element through the tissue. The tissue retractor may be independently movable relative to the cutting element. The tissue retractor may include a tissue collection element that collects tissue cut by the cutting element. The tissue retractor may be positioned adjacent a radially inner side of the cutting element when the tissue retractor and cutting element are in the bowed positions. The tissue retractor may include a membrane, whereby the membrane provides the thickened portion when in a collapsed configuration. The thickened portion may be at least two times larger than a cutting element thickness. The thickened portion may be at least three times larger than a cutting element thickness. The thickened portion may be spaced from the cutting side by a distance of less than 0.25 inch. The device may further include a tissue collection element that trails the cutting element to collect tissue cut by the cutting element. The thickened portion may be formed at least in part by an electrical insulation that covers part of the cutting element. A side of the RF cutting element opposite the cutting side may be insulated so that RF energy is not delivered to the tissue from the side opposite the cutting side. The thickened portion may retract tissue away from a radially inner surface of the cutting element when the cutting element is in the bowed position. The thickened portion may retract tissue away from a radially outer surface of the cutting element when the cutting element is in the bowed position. The thickened portion may retract tissue away from both a radially inner surface and a radially outer surface of the cutting element when the cutting element is in the bowed position.

According to still another embodiment thereof, the present invention is a method of removing breast tissue, comprising the steps of providing a tissue cutting device having an elongate cutting element coupled to a shaft, the cutting element being movable between a bowed position and a retracted position, a deployed part of the cutting element lies outside the shaft when in the bowed position, the deployed part of the cutting element having a cutting side that penetrates the tissue as the shaft may be rotated; introducing the tissue cutting device into a breast; coupling a power source to the elongate cutting element; moving the elongate cutting element to the bowed position so that the deployed part of the cutting element lies outside the shaft; preventing energy from being transmitted from a portion of the deployed part of the cutting element to the tissue while the elongate cutting element may be in the bowed position; and rotating the cutting device so that the cutting side of the bowed cutting element penetrates the breast tissue to cut the breast tissue for removal.

The preventing step may be carried out by preventing energy from being transmitted from a radially inner portion of the cutting element to the tissue. The preventing step may be carried out by partially covering the deployed part of the cutting element. The preventing step may be carried out by partially covering the deployed part of the cutting element with insulation that prevents transmission of energy to the tissue. The preventing step may be carried out by covering the deployed part of the cutting element with an element that is also movable between bowed and retracted positions. The preventing step may be carried out with the element positioned adjacent a radially inner side of the cutting element. The preventing step may be carried out with a tissue collection element preventing contact between the tissue and the portion of the cutting element; and the rotating step may be carried out to sever tissue that is collected by the tissue collection element. The preventing step may be carried out with the portion of the cutting element not transmitting energy to the tissue being primarily on a trailing side of the cutting element.

The present invention is also a device for removing tissue, comprising a shaft; a cutting element coupled to the shaft, the cutting element being movable between a bowed position and a retracted position, a deployed part of the cutting element lies outside the shaft when in the bowed position, the deployed part of the cutting element having a cutting side that penetrates the tissue as the shaft may be rotated, the cutting element having means for preventing energy for cutting tissue from being transmitted from a portion of the deployed part of the bowed cutting element to the tissue. The preventing means may prevent energy from being transmitted from a radially inner portion of the cutting element to the tissue. The preventing means partially covers the deployed part of the cutting element. The preventing means may include insulation that partially covers the deployed part of the cutting element. The preventing means may cover the deployed part of the cutting element with an element that is also movable between bowed and retracted positions. The preventing means may include an element positioned adjacent a radially inner side of the cutting element. The preventing means may include a tissue collection element that prevents contact between the tissue being cut and the portion of the cutting element, the tissue collection element collecting the tissue being cut by the cutting element. The preventing step means may prevent transmission of energy to the tissue primarily from a trailing side of the cutting element that is opposite the cutting side.

The present invention is also a device for removing breast tissue, comprising a shaft; a cutting element mounted to the shaft, the cutting element being movable between a bowed position and a straightened position, the cutting element bowing outward away from the shaft when in the bowed position, the cutting element having an elongate cutting side that cuts tissue when the shaft may be rotated, the cutting element having a length that may be at least 25 times larger than a width of the cutting element.

The cutting element may have an exposed surface area for transmitting energy to the tissue being cut, the exposed surface area including a radially inner part and a radially outer part, the radially outer part being larger than the radially inner part. Only one cutting element may be mounted to the shaft. The cutting element may have a rectangular cross-sectional shape. The device may further include a tissue collection element coupled to the cutting element and/or the shaft, the tissue collection element collecting tissue that is severed by the cutting element. The length of the cutting element may be at least 40 times larger than the width of the cutting element. The length of the cutting element may be at least 100 times larger than the width of the cutting element. The cutting element may have an effective width that is less than the width of the cutting element, the effective width being a width that is exposed for contact with the tissue being cut to transmit cutting energy to the tissue. The length of the cutting element may be at least 25 times larger than the effective width thereof. The length of the cutting element may be at least 40 times larger than the effective width thereof. The length of the cutting element may be at least 100 times larger than the effective width thereof.

The present invention, according to yet another embodiment thereof, is a method of cutting breast tissue for removal, comprising the steps of providing a tissue cutting device having an elongate cutting element, the cutting element being movable between a bowed position and a retracted position, the cutting element having a radially outer side and a radially inner side; introducing the tissue cutting device into a breast; moving the elongate cutting element to the bowed position; coupling a power source to the elongate cutting element; and rotating the cutting element after the moving step so that the cutting element cuts the breast tissue, the radially outer side has a larger surface area for transmitting energy to cut the tissue than the radially inner side.

The rotating step may be carried out with the radially outer side having an exposed part for transmitting energy to the tissue that is at least 20% larger than an exposed part of radially inner side for transmitting energy to the tissue. The rotating step may be carried out with the radially outer side having an exposed part for transmitting energy to the tissue that is at least 35% larger than an exposed part of radially inner side for transmitting energy to the tissue. The rotating step may be carried out while partially covering at least part of the radially inner side of the cutting element. The rotating step may be carried out with a cover positioned adjacent the cutting element, the cover also being movable between bowed and retracted positions. The preventing step may be carried out with the cover positioned adjacent a radially inner side of the cutting element. The preventing step may be carried out with the portion of the cutting element not transmitting energy to the tissue being primarily on a trailing side of the cutting element. The preventing step may be carried out with a tissue collection element preventing contact between the tissue and the portion of the cutting element; and the rotating step may be carried out to sever tissue that is collected by the tissue collection element. The preventing step may be carried out by insulating part of the deployed part of the cutting element to prevent transmission of energy to the tissue.

The present invention, according to another embodiment thereof, is a device for cutting breast tissue for removal, comprising a shaft; and an elongate cutting element mounted to the shaft, the cutting element being movable between a bowed position and a retracted position, the cutting element having a radially outer side and a radially inner side, the radially outer side has a larger surface area for transmitting energy to cut the tissue than the radially inner side.

The radially outer side may have an exposed part for transmitting energy to the tissue that is at least 20% larger than an exposed part of radially inner side for transmitting energy to the tissue. The radially outer side may have an exposed part for transmitting energy to the tissue that is at least 35% larger than an exposed part of radially inner side for transmitting energy to the tissue. The radially inner side of the cutting element may be partially covered. The radially inner side may be covered by a cover positioned adjacent the cutting element, the cover also being movable between bowed and retracted positions. The partially covered portion of the cutting element may be on a trailing side of the cutting element. The device may also include a tissue collection element for collecting tissue severed by the cutting element. The cutting element may have a deployed part lying outside the shaft in the bowed position; at least part of the cutting element may be covered with insulation.

According to another embodiment thereof, the present invention is a device for cutting and collecting a specimen from a mass of tissue, comprising an integrated cut and collect assembly, the integrated cut and collect assembly including a cutting portion and a collection portion that includes a flexible membrane, the collection portion being attached to the cutting portion, the cutting portion being configured to cut the specimen from the mass of tissue and the collection portion being configured to collect the cut specimen and to isolate the cut specimen within the membrane.

Alternatively, the present invention may be viewed as a method of cutting and isolating a specimen from a mass of tissue, comprising the steps of inserting an instrument that includes an integrated cut and collect assembly into the mass of tissue, the integrated cut and collect assembly including a cutting portion and a collection portion that includes a thin flexible membrane, the collection portion being attached to the cutting portion, the cutting portion being configured to cut the specimen from the mass of tissue and the collection portion being configured to collect the cut specimen from the mass of tissue and to isolate the cut specimen from the mass of tissue within the membrane, isolating the specimen from surrounding tissue by cutting the specimen from the mass of tissue with the cutting portion and collecting the cut specimen within the flexible membrane of the collecting portion.

A device for cutting and collecting a specimen from a mass of tissue, according to still another embodiment of the present invention, includes a shaft defining a proximal and a distal end; a work assembly near the distal end of the shaft, the work assembly being configured to cut the specimen from the mass of soft tissue and to isolate the cut specimen from surrounding tissue; and a single actuator near the proximal end of the shaft, the single actuator being mechanically coupled to the work assembly such that rotation of the device and operation of the single actuator is effective to cut, collect and isolate the specimen from the mass of tissue as the device is rotated.

A method of collecting a tissue specimen from a mass of tissue, includes steps of inserting a surgical instrument into the mass of tissue to a target location within the mass of tissue, the instrument including a shaft and a work assembly near a distal end of the shaft, the work assembly being configured to controllably cut the specimen from the mass of soft tissue and to isolate the cut specimen from the mass of tissue within a tissue isolator; controlling the work assembly of the surgical instrument to cut and isolate the specimen, and retracting the instrument from the mass of tissue while the specimen is isolated within the tissue isolator and at least partially trails the distal end of the shaft.

Lastly, a surgical instrument for retrieving a tissue specimen from a mass of tissue, according to another embodiment, includes a shaft defining a proximal and a distal end, and a work assembly coupled to the shaft near the distal end thereof, the work assembly including: a tissue cutting portion configured to cut the tissue specimen from the mass of tissue; a tissue collection portion that includes a membrane, the membrane being configured to encapsulate and isolate the cut specimen from the mass of tissue and being adapted to stretch to enable the encapsulated specimen to at least partially trail the distal end of the shaft as the surgical instrument is retracted from the mass of tissue. According to an embodiment thereof, the present invention is a device for cutting and collecting a specimen from a mass of tissue. The device includes an integrated cut and collect assembly, the integrated cut and collect assembly including a cutting portion and a collection portion that includes a flexible membrane, the collection portion being attached to the cutting portion. The cutting portion is configured to cut the specimen from the mass of tissue and the collection portion is configured to collect the cut specimen and to isolate the cut specimen within the membrane.

The device may further include a shaft and an actuator, the integrated cut and collect assembly being coupled to the shaft, the assembly being coupled to the actuator such that operation of the actuator causes a deployment of the integrated assembly from a retracted position at least partially within the shaft to a selectable expanded position away from the shaft. The integrated cut and collect assembly may assume a bowed shape in the expanded position. The thin flexible membrane may be configured to at least partially encapsulate the cut specimen. For example, the flexible membrane may be configured to encapsulate at least 40% of the surface area of a specimen. The cutting portion may define a cutting edge and a trailing edge and the collection portion of the integrated cut and collect assembly may extend from the trailing edge to the shaft. The thin flexible membrane portion may further include an inorganic elastomer. The integrated cut and collect assembly may further include an RF cutting portion. The cutting portion may be configured to be energized by an RF energy source.

The flexible membrane may be substantially non-conductive in tissue and may further include an RF-resistant material. The flexible membrane may include a polymeric material. The polymeric material may include an organic, inorganic or organic-inorganic polymer. For example, the polymeric material may include a silicone or silicone-containing elastomer. The flexible membrane may also include one or more of the following materials: a teraphthalate, a tetrafluoroethylene, a polytetrafluoroethylene, a polyimid, a polyester, Kevlar® and/or M5® fibers (a proprietary rigid rod polymer manufactured by Magellan Systems International, LLC of Bethesda, Md.), for example. The flexible membrane may have a laminar structure that may further include a reinforcing layer. There is preferably an intervening layer of silicone elastomer or silicone-containing elastomer between the point(s) of contact with the energized cutting portion and the reinforcing layer. The reinforcing layer should preferably have a higher tensile strength and/or greater tear resistance than the polymeric material (such as a silicone or silicone containing elastomer) of the membrane. The reinforcing layer may further include, for example, a polyester, a polyimid, a polyurethane, a polyolephin (such as a polyethylene, for example). The flexible membrane may be shaped like a bag and may be fluid-tight and/or semi-porous. Such a membrane 114, therefore, is interposed between the cut specimen and the surrounding tissue, thereby physically isolating (by means of the continuous, homogeneous and fluid tight membrane 114) the cut and collected specimen from the surrounding tissue.

The actuator may be effective to simultaneously operate the cutting and the collection portions of the integrated cut and collect assembly such that expansion of the cutting portion causes an expansion of the collection portion of the integrated cut and collect assembly. The integrated cut and collect assembly may be configured as a single loop that selectively expands and retracts upon operation of the actuator.

The cutting portion may further include a braided leading edge. The cutting portion may define a braided metallic tube or a portion thereof. The collecting portion may be attached to the braided metallic tube. The cutting portion may further include a metallic braided cutter disposed around a mandrel that supports the collection portion of the integrated cut and collect assembly. The collection portion may define a flexible membrane that may further include a locally thicker portion (e.g., bulbous portion) around which the cutting portion may be crimped or otherwise attached. The cutting portion may further include first and second metallic ribbons disposed so as to sandwich a portion of the flexible membrane therebetween. The first metallic ribbon may be attached to the second metallic ribbon through rivets, welds and/or pins, for example. The cutting portion may further include a metallic ribbon and the flexible membrane may be sewn onto the metallic ribbon. The cutting portion may further include a flat flexible metallic ribbon that defines a plurality of windows defining a centerline, and the flat metallic ribbon may be bent at the centerline around a portion of the collection portion. The cutting portion may further include a first ribbon and the thin flexible membrane may be attached to a second ribbon, both the first and second ribbon being mechanically coupled to one another and to the actuator. The second ribbon may be coupled to an RF energy source. The second ribbon may be disposed so as to at least partially overlap the first ribbon. The device may further include a mechanical coupling between the first and second ribbons. The cutting portion may have a generally cylindrical shape that defines an internal lumen in which a first part of the collection portion may be secured, a remaining part of the collection portion emerging from a slot defined in the cutting portion and being attached to the shaft. A flexible mandrel may be disposed within the internal lumen of the cutting portion, the first part of the flexible membrane being wrapped around the mandrel, a length of the mandrel being larger than a length of the slot. The device may further include an inflatable balloon disposed on and/or about the shaft. The inflatable balloon may be configured to be inflated by a gas or a liquid. The inflatable balloon may be configured to be inflated by a gas and/or a fluid. The balloon may be configured to massage the mass of tissue by pulsating the inflation of the balloon. Such massaging may aid in dispersing the anesthetic used during the excisional procedure. The inflatable balloon may be configured as a cooling sleeve and/or as a tissue expander. The inflatable balloon may be configured to stabilize the device when inserted in tissue, to seal the incision through which the device is inserted, to provide hemostatis and/or to reduce capacitive coupling to reduce tissue heating.

The integrated cut and collect assembly may be single use and disposable. The shaft and the integrated cut and collect assembly may be single use and disposable, as may be the entire device itself.

The membrane of the collection portion may be configured so as to enable the collected and isolated specimen to at least partially trail behind the device as the device is retracted from the mass of tissue. The cutting portion may further include a first ribbon and the collecting portion may further include a second ribbon and a tube encircling at least a portion of the second ribbon, the thin flexible membrane being attached to the tube and to an exterior surface of the device, both the first and second ribbon being mechanically coupled to one another and to the actuator. The flexible membrane may be attached to the collection portion by an adhesive, such as a cyanoacrylate, for example. The shaft may define a trough in which the integrated cut and collect assembly may at least partially retract. The trough may be configured to separate the integrated cut and collect assembly from the tissue to be cut when the integrated assembly is in the retracted position. The trough may also be configured to enable the cutting portion to become fully energized before coming into contact with the tissue to be cut. The trough may also be configured to reduce thermal damage to the tissue to be cut while the cutting portion is energizing (while in the trough). The shaft may define a trough and the membrane may be disposed over the trough and attached to the shaft. The cut and collect assembly may then be configured so as to stretch the membrane open and closed as the cut and collect assembly is expanded and retracted, respectively. The cut and collect assembly may include a single ribbon that is split into a cutting portion and a collecting portion, the membrane being attached to the collecting portion and to the shaft.

According to another embodiment thereof, the present invention is a method of cutting and isolating a specimen from a mass of tissue, comprising the steps of inserting an instrument that may include an integrated cut and collect assembly into the mass of tissue, the integrated cut and collect assembly including a cutting portion and a collection portion that may further include a thin flexible membrane, the collection portion being attached to the cutting portion. The cutting portion may be configured to cut the specimen from the mass of tissue and the collection portion may be configured to collect the cut specimen from the mass of tissue and to isolate the cut specimen from the mass of tissue within the membrane. The method also includes the steps of isolating the specimen from surrounding tissue by cutting the specimen from the mass of tissue with the cutting portion and collecting the cut specimen within the flexible membrane of the collecting portion.

The isolating step may further include a step of drawing the flexible membrane around the cut specimen. The flexible membrane in the inserting and isolating steps may include a polymeric material (such as, for example, an organic, inorganic or organic-inorganic polymer). The membrane may include a silicone or silicone-containing elastomer. The membrane may also include a teraphthalate, a tetrafluoroethylene, a polytetrafluoroethylene, a polyimid, a polyester, a polyurethane, a polyolephin (such as polyethylene, for example), Kevlar® and/or M5® fiber, for example. The flexible membrane in the inserting and isolating steps may be shaped like a bag (of a shape effective to collect and isolate the cut specimen) and may be fluid tight. The isolating step may further include a step of energizing the cutting portion using an RF energy source. The isolating step may further include cutting a margin of healthy tissue around the specimen. The isolating step may preserve the tissue architecture of the cut, collected and isolated specimen. The instrument may define a longitudinal axis and the isolating step may be carried out while rotating the instrument about the longitudinal axis. The isolating step may be carried out to physically isolate the specimen from surrounding tissue so that the cut and collected specimen does not contact the surrounding tissue from which the specimen has been cut. The isolating step may be carried out with the collection portion of the integrated cut and collect assembly expanding to a size at least as large as a size of the specimen. The instrument defines a longitudinal axis and the inserting step may further include positioning the instrument such that the specimen to be cut is adjacent the cutting portion and the isolating step may be carried out by rotating the instrument about the longitudinal axis so that the cutting portion cuts the specimen and the isolating step collects and isolates the cut specimen within the flexible membrane. The instrument further may further include a shaft and an actuator, the integrated cut and collect assembly being coupled to the shaft, the assembly being coupled to the actuator such that operation of the actuator causes a deployment of the integrated assembly from a retracted position at least partially within the shaft to a selectable expanded position away from the shaft. The isolating step may be initiated by acting upon the actuator to cause a simultaneous deployment of both the cutting and collecting portions of the integrated cut and collect assembly. The instrument further may further include an inflatable balloon disposed proximal to the integrated cut and collect assembly and the method further may further include inflating the balloon. The inflating step may be carried after the inserting step.

The present invention may also be viewed as a device for cutting and collecting a specimen from a mass of tissue, comprising a shaft defining a proximal and a distal end; a work assembly near the distal end of the shaft, the work assembly being configured to cut the specimen from the mass of soft tissue and to isolate the cut specimen from surrounding tissue; a single actuator near the proximal end of the shaft, the single actuator being mechanically coupled to the work assembly such that rotation of the device and operation of the single actuator is effective to cut, collect and isolate the specimen from the mass of tissue as the device is rotated.

The device may define a longitudinal axis and the actuator may be configured to, for example, selectively slide along the longitudinal axis to selectively deploy and retract the work assembly, although other actuation mechanisms are possible. The work assembly may be configured to be energized by an RF energy source. According to this embodiment, sliding the actuator toward the distal end deploys the work assembly and sliding the actuator in the proximal position retracts the work assembly. The work assembly may be configured so that the collected specimen is isolated from the mass of tissue when the actuator is slid in the proximal position and the work element is retracted.

According to another embodiment thereof, the present invention is also a method of collecting a tissue specimen from a mass of tissue, comprising the steps of inserting a surgical instrument into the mass of tissue to a target location within the mass of tissue, the instrument including a shaft and a work assembly near a distal end of the shaft, the work assembly being configured to controllably cut the specimen from the mass of soft tissue and to isolate the cut specimen from the mass of tissue within a tissue isolator; controlling the work assembly of the surgical instrument to cut and isolate the specimen, and retracting the instrument from the mass of tissue while the specimen is isolated within the tissue isolator at least partially trails the distal end of the shaft.

The method may further include a step of making an incision into the mass of tissue prior to the inserting step, the instrument creating an insertion path defined between the incision and the target location and the isolated specimen trails the distal end of the shaft within the insertion path during the retracting step. A step of making an incision into the mass of tissue prior to the inserting step may be carried out. The incision making step makes an incision that may be only as large as needed to enable insertion of the distal end of the shaft into the mass of tissue. The retracting step retracts the isolated specimen from the tissue mass without substantially enlarging the incision.

The present invention is also a surgical instrument for retrieving a tissue specimen from a mass of tissue, comprising a shaft defining a proximal and a distal end, and a work assembly coupled to the shaft near the distal end thereof, the work assembly including a tissue cutting portion configured to cut the tissue specimen from the mass of tissue; a tissue collection portion that may further include a membrane, the membrane being configured to encapsulate and isolate the cut specimen from the mass of tissue and to being adapted to stretch to enable the encapsulated specimen to at least partially trail the distal end of the shaft as the surgical instrument is retracted from the mass of tissue.

The tissue cutting portion may be configured to be energized with RF energy and the membrane may include an RF resistant material (e.g., a material that resists the temperature of the RF-energized cutting portion). The membrane may include a polymeric material. The membrane may include an organic, inorganic or organic-inorganic polymer such as a silicone elastomer or a silicone-containing elastomer. The membrane may also include a teraphthalate, a tetrafluoroethylene, a polytetrafluoroethylene, a polyimid, a polyester, a polyurethane, a polyolephin (such as a polyethylene, for example), Kevlar® and/or M5® fiber, for example. The tissue collection portion may be selectably expandable and retractable (in a radial direction, for example) relative to the shaft. The tissue cutting portion may be selectably expandable and retractable in a radial direction relative to the shaft. The membrane may have a laminar structure that may further include a reinforcing layer. The membrane may be shaped like a bag, which may be fluid-tight, non-porous or semi-porous. The membrane may also include a woven and coated layer.

BRIEF DESCRIPTION OF THE DRAWINGS

For a further understanding of the objects and advantages of the present invention, reference should be made to the following detailed description, taken in conjunction with the accompanying figures, in which:

FIG. 1A is perspective view of an excisional device according to an embodiment of the present invention.

FIG. 1B is a partial enlarged view of the excisional device of FIG. 1A, in which the integrated cut and collect assembly thereof is in an expanded configuration.

FIG. 1C shows the device of FIG. 1B with an element for retracting tissue away from the ribbon 116.

FIG. 2A is a cross-sectional side view of an excisional device according to an embodiment of the present invention.

FIG. 2B is a perspective view of a portion of the integrated cut and collect assembly of FIG. 2A.

FIG. 2C is a perspective view of the collection portion of the integrated cut and collect assembly, showing the manner in which the flexible membrane may be attached to the assembly and the outer surface of the shaft of the present excisional device, according to an embodiment of the present invention.

FIG. 2D is a cross-sectional view showing the relative positions of the ribbons.

FIG. 2E shows an alternative view of FIG. 2D along the cross-section of FIG. 1B.

FIG. 2F shows another alternative view of FIG. 2D.

DESCRIPTION OF THE INVENTION

Figure 3:
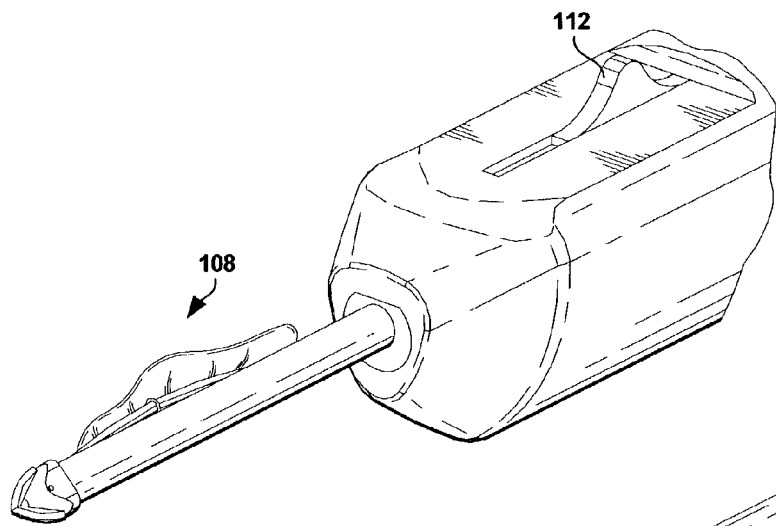
FIG. 3 is a perspective view of an excisional device according to an embodiment of the present invention, with the integrated cut and collect assembly in the retracted position.

FIG. 1A is a perspective view of an excisional device according to an embodiment of the present invention. As shown, the excisional device 100 includes a proximal section 102 that may be configured to fit the physician's hand. Extending from the proximal section 102 is a shaft 104 that may be terminated by a distal tip 106. However, an introducer may be used for the initial incision, whereupon the tip 106 may be omitted from the device 100. The distal tip 106 is configured so as to easily penetrate a mass of tissue, and may feature curvilinear cutting surfaces (best seen in FIG. 1B). The distal tip 106 may be configured to be energized by a radio frequency (RF) energy source, supplied via the electrical cord 122. However, the distal tip 106 need not be energized, as the sharpness of the cutting surfaces of the distal tip 106 is generally sufficient to easily penetrate the tissue to the target excision site. The distal tip 106 may be configured to be retractable and extendable, so as to reduce trauma. An integrated cut and collect assembly 108 is mounted near the distal tip 106 or near the distal most portion of the shaft 104. According to the present invention, the integrated cutting and collection assembly 108 is configured to cut a tissue specimen (a piece of tissue or a lesion) from the mass of tissue (such as, for example, breast tissue), to collect the cut specimen and to isolate the cut specimen from the surrounding tissue by, for example, encapsulating the same within a flexible bag-shaped membrane. Although the present invention finds advantageous utility in terms of excisional procedures on the female breast, it is understood that the present invention is not limited thereto. Indeed, the present methods and devices may be advantageously employed and deployed within most any mass of soft tissue. Moreover, although the present excisional device described and shown herein is presented as a hand held excisional device, it is to be understood that the proximal section 102 may be suitably modified to fit within a stereotactic unit for automated, semi-automated or manual operation.

According to the present invention, the integrated cut and collect assembly 108 includes a cutting portion and a collection portion that includes a flexible membrane 114. The collection portion of integrated cut and collect assembly 108 is attached to the cutting portion. As shown most clearly in FIG. 1B, the collection portion may be attached to the cutting portion, according to an embodiment of the present invention, by a small ring member 124 encircling both the cutting portion and part of the collecting portion so as to insure that the cutting and collection portions of the integrated cut and collect assembly 108 move together. As noted above, the cutting portion is configured to cut the specimen from the mass of tissue and the collection portion is configured to collect the cut specimen and to isolate the cut specimen from surrounding tissue. This isolation from surrounding tissue, according to the present invention, is carried out by a flexible membrane 114 that forms a part of the collecting portion of the integrated cut and collect assembly 108, as described in detail below.

The integrated cut and collect assembly 108 may be mechanically coupled to an actuator 112 such that operation of the actuator 112 causes a deployment of the integrated cut and collect assembly 108 from the retracted position shown in FIG. 1A in which the integrated cut and collect assembly 108 is at least partially retracted within a trough 120 defined within the shaft 104 to a selectable expanded position away from the shaft 104, as shown in FIG. 1B. For example, by pushing the actuator 112 in the distal direction (i.e., toward the distal tip 106), the integrated cut and collect assembly 108 transitions from the retracted position shown in FIG. 1A to a selectable variable expanded position illustrated in FIG. 1B in which the integrated cut and collect assembly 108 bows out radially relative to the longitudinal axis of the shaft 104 (i.e., in the direction of arrow 110 in FIG. 1A). The degree of bowing (expansion) of the integrated cut and collect assembly 108 depends upon the travel imposed upon the actuator 112 by the physician. In this manner, the physician may match the degree of expansion of the integrated cut and collect assembly 108 to the size of the targeted lesion or the size of the desired specimen within the mass of tissue. The degree of expansion may be varied at will during the excisional procedure by means of direct observation by means of ultrasound or some other imaging or guidance modality disposed within the shaft 104 or external to the device 100.

The cutting portion may include a ribbon 116 that is pushed out of the trough 120 to assume the bowed shape of FIG. 1B. The ribbon may be energized by an RF energy source so as to efficiently cut the specimen from the mass of tissue. A standard, off the shelf and widely available RF generator, such as a ValleyLab Force FX Generator from ValleyLab of Boulder, Colo. may advantageously be used to energize the cutting portion of the integrated cut and collect assembly 108 of the present invention, although other RF generators may also be employed to energize the cutting portion of the integrated cut and collect assembly 108 and/or the tip 106 described herein. As the excisional device is rotated during the cutting of the specimen, the ribbon 116 of the cutting portion preferably forms the leading edge of the integrated cut and collect assembly 108. The collecting portion of the integrated cut and collect assembly 108 may also include a ribbon that is mechanically coupled to the cutting portion thereof, shown in FIG. 1B at reference numeral 118. The ribbon 118 of the collecting portion may at least partially overlap the ribbon 116 of the cutting portion. Attached to the collecting ribbon 118 and/or to the ribbon 116 of the cutting portion is a flexible membrane 114, which serves to collect and to isolate the collected specimen by drawing over the cut specimen and encapsulating same. The flexible membrane 114 may be shaped as a bag (a container that is closed on all sides except a selectively openable and closable opening) whose opening may be attached to both the shaft 104 and the collecting ribbon 118 and/or the ribbon 116 of the cutting portion of the integrated cut and collect assembly 108. Although the embodiment of the present invention shown in FIGS. 1A and 1B includes a cutting ribbon 116 and a collecting ribbon 118, both ribbons are expanded and retracted substantially simultaneously as they are mechanically coupled to one another to form the integrated cut and collect assembly 108, a single mechanical expandable and retractable loop. Alternatively, only a single ribbon may be present and the flexible membrane attached directly to such single ribbon, as detailed herein below. By virtue of this configuration, when the integrated cut and collect assembly 108 is in the expanded position (FIG. 1B), the bag is in an open configuration in which the tissue cut by the cutting portion is received and collected in the bag formed by the flexible membrane 114 as the device is rotated. However, when the integrated cut and collect assembly 108 is in the retracted position (FIG. 1A), the opening of the bag formed by the flexible membrane 114 is pinched shut or substantially shut, thereby trapping and encapsulating the collected specimen therein and isolating (or substantially isolating) the collected specimen from the surrounding tissue.

FIG. 2A is a cross-sectional side view of an excisional device according to an embodiment of the present invention. As shown, the actuator 112 may be mechanically coupled to the integrated cut and collect assembly 108 so that when the actuator is pushed in the proximal direction, the integrated cut and collect assembly 108 retracts within the trough 120 defined within the shaft 104. Conversely, when the actuator 112 is pushed in the distal direction, the integrated cut and collect assembly 108 is pushed out of the trough 120 and expands out of the trough 120 to assume the bowed shape shown in FIG. 2A. The ribbon or ribbons of the integrated cut and collect assembly 108 may extend back to the actuator 112 through a first lumen 204 defined within the shaft 104 and may be attached to the actuator 112 to thereby enable movement of the actuator 112 to expand and retract the integrated cut and collect assembly 108. Alternatively, the ribbon 118 of the collecting portion of the integrated cut and collect assembly 108 may only extend a fraction of the length of the cutting ribbon 116. However, as the two ribbons are mechanically coupled to one another, expansion of the cutting ribbon 116 causes the simultaneous expansion of the collecting ribbon 118 without the collecting ribbon 118 being directly attached to the actuator 112.

A second lumen 206 may also be defined within the shaft 104. The second lumen 206 may be used, for example, to evacuate smoke and/or bodily fluids from the excision site within the mass of tissue. Alternatively the second lumen 206 defined within the shaft 104 may be used to deliver a pharmaceutical agent to the excisional site, such as, for example, an anesthetic, an analgesic and/or some other agent. Other uses may be found for such lumen. An inflatable balloon 208 may be coupled to the shaft 104. The balloon 208 may be inflated with, for example, a gas (air, an inert gas or carbon dioxide, for example) or a fluid such as saline. The balloon may serve several functions. For example, the balloon 208 may be configured to massage the mass of tissue by pulsating the inflation of the balloon, may be configured as a cooling sleeve, may be configured as a tissue expander, may be configured to stabilize the device when inserted in tissue, may be configured to seal the incision through which the device is inserted, to provide hemostatis, and/or to reduce capacitive coupling to reduce tissue heating. The balloon 208 may be inflated from a lumen defined within the excisional device and supplied to the device via a suitable port defined in the proximal end of the device. The actuator 112 may define one or more protrusions 212 and an interior surface of the device may include corresponding crenellations that are collectively and cooperatively configured to provide a number of set stops to the actuator 112 along its travel path and optionally a tactile feedback for the physician, who can set the integrated cut and collect assembly 108 to predetermined degrees of expansion without looking at the device during the excisional procedure. Indeed, during the procedure, as the physician expands the integrated cut and collect assembly 108, he or she will feel periodic increases in resistance followed by a tactile and/or audible release as the protrusions 212 slip into the crenellations 210.

FIG. 2B is a perspective view of a detail of the integrated cut and collect assembly 108 of FIG. 2A. According to this embodiment, the cutting ribbon includes a first cutter ribbon 116A and a second cutter ribbon 116B that may be welded (or otherwise attached) to the first cutter ribbon 116A, as shown by weld 252. Together, the first cutter ribbon 116A and the second cutter ribbon 116B constitute the leading (and cutting) edge of the integrated cut and collect assembly 108. Behind this leading edge is the collecting portion of the integrated cut and collect assembly 108. Specifically, behind the leading edge of the cutting portion is disposed the ribbon 118 to which the flexible membrane 114 is attached. The ribbon 118 to which the flexible membrane 114 is attached may also be welded (or otherwise attached) to the first cutter ribbon 116A, as also shown at 252. The first ribbon 116A may be relatively wider than the second ribbon 116B, so as to completely overlap both the second ribbon 116B and the ribbon 118 to which the flexible membrane 114 is attached. This gives the integrated cut and collect assembly 108 necessary rigidity, while allowing the second ribbon 116B and the ribbon 118 to be reduced in size, thereby reducing space and bulk. The three ribbons 116A, 116B and 118 are preferably kept at a voltage equipotential, so as to decrease the possibility of arcing when RF power is applied to the integrated cut and collect assembly 108. According to an advantageous embodiment of the present invention, only the first ribbon 116A need be coupled to the actuator 112. As the second ribbon 116B and the ribbon 118 are mechanically coupled to the first ribbon 116A, they will move in unison with the first ribbon 116A as the actuator 112 is moved by the physician or the stereotactic unit to which the device 100 may be coupled. The device may, of course, omit one of the ribbons 116A, 116B such as ribbon 116B as shown in FIGS. 2E and 2F leaving only ribbon 116A for cutting tissue. The description of ribbon 116 as used herein shall apply to ribbon 116A and/or ribbon 116B as shown in FIGS. 2C, 2E and 2F as applicable.

FIG. 2C is a perspective view of the collection portion of the integrated cut and collect assembly, showing the manner in which the flexible membrane 114 may be attached within the assembly 108 and to the outer surface of the shaft 104 of the present excisional device 100, according to an embodiment of the present invention. As shown therein, the flexible membrane 114 may include a lumen forming portion 224 through which the ribbon 118 (see FIG. 2B) is inserted, to provide rigidity to the mouth or opening 222 of the collecting portion of the integrated cut and collect assembly 108. The ribbon 118 is attached to the cutting ribbon 116 (116A, 116B) so as to expand and retract therewith under the action of the actuator 112. The flexible membrane 114 also includes a shaft attachment tab 220, which is configured to attach the flexible membrane 114 to the shaft 104 of the present excisional device. For example, the shaft attachment tab 220 may be attached to the shaft 104 through a mechanically and biologically appropriate adhesive. The remainder of the flexible membrane 114 may be shaped as a bag, the opening or mouth 222 thereof being delimited by the shaft attachment tab 220 and the lumen forming portion 225 through which the ribbon 118 runs. Therefore, when the actuator 112 causes the integrated cut and collect assembly 108 to expand, the opening 222 of the integrated cut and collect assembly 108 is opened and when the actuator 112 causes the integrated cut and collect assembly 108 to retract at least partially within the shaft 104, the mouth 222 of the bag formed by the flexible membrane 114 closes, effectively encapsulating and isolating whatever tissue, specimen or lesion has been cut and collected therein. The tissue is isolated, as the lumen forming portion 224, when the integrated cut and collect assembly 108 is in the retracted state, may be pressed against the shaft 104, thereby interposing a layer of the flexible membrane 114 between the collected tissue and the surrounding tissue.

As an alternative, the flexible membrane 114 may be attached to an exterior surface of the device 100 and to a tube defining a lumen running at least a portion of the length of the second ribbon 118. The flexible membrane may be attached thereto by means of an adhesive, for example. Other means and structures for attaching the flexible membrane 114 to the cutting portion of the integrated cut and collect assembly 108 are disclosed herein below.

FIG. 2D is a perspective view of a shaft 104 of the present excisional device, showing further aspects thereof. As shown therein, the shaft 104 defines a trough 120 near the distal end thereof. Preferably, the trough 120 includes a ledge portion 121 that is cut out of the shaft 104. The ledge 121 allows additional room to accommodate the membrane 114 when the integrated cut and collect assembly 108 retracts within the trough 120. The ledge 121 within the trough 120 enables the integrated cut and collect assembly 108 to more fully retract within the trough 120 than would otherwise be possible without the ledge 121 by providing additional space for the membrane 114. Without the ledge 121, the bulk of the membrane 114 could hamper the full retraction of the integrated cut and collect assembly 108 into the trough 120. The integrated cut and collect assembly 108 is preferably at least partially retracted within the trough 120 when the cutting portion thereof is first energized, prior to initiating cutting of tissue. This separates the tissue to be cut from the cutting portion of the integrated cut and collect assembly 108 until the assembly has been sufficiently energized to efficiently cut through the tissue. The trough 120 is also instrumental is allowing the present excisional device to utilize a standard RF generator (e.g., one that does not rely upon feedback from an impedance sensor or the like to vary the applied power), such as the ValleyLab Force FX Generator discussed above. Keeping the integrated cut and collect assembly 108 at least partially retracted within the trough 120 also prevents excessive thermally-induced tissue damage, as all or most of the surface area of the cutting portion of the integrated cut and collect assembly 108 is kept away from the tissue until the cutting portion is fully energized (i.e., until the current density at the cutting portion of the integrated cut and collect assembly 108 is sufficient to initiate and maintain arcing). Other means and structures for enabling the RF cutting portion of the integrated cut and collect assembly 108 are disclosed in commonly assigned and co-pending U.S. application Ser. No. 09/732,848 filed on Dec. 7, 2000, the disclosure of which is hereby incorporated herein in its entirety.

Figure 4:
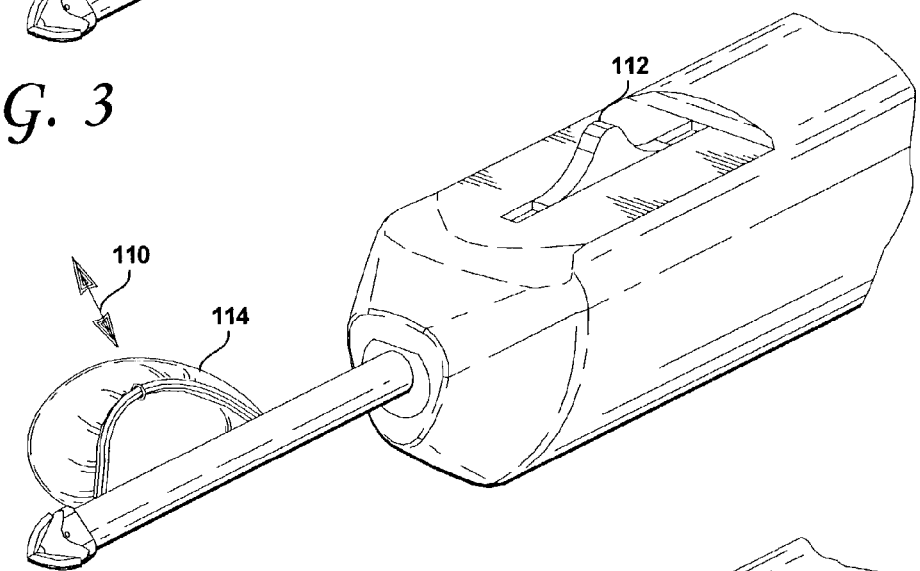
FIG. 4 shows the excisional device of FIG. 3, with the integrated cut and collect assembly in an expanded position.
Figure 5:
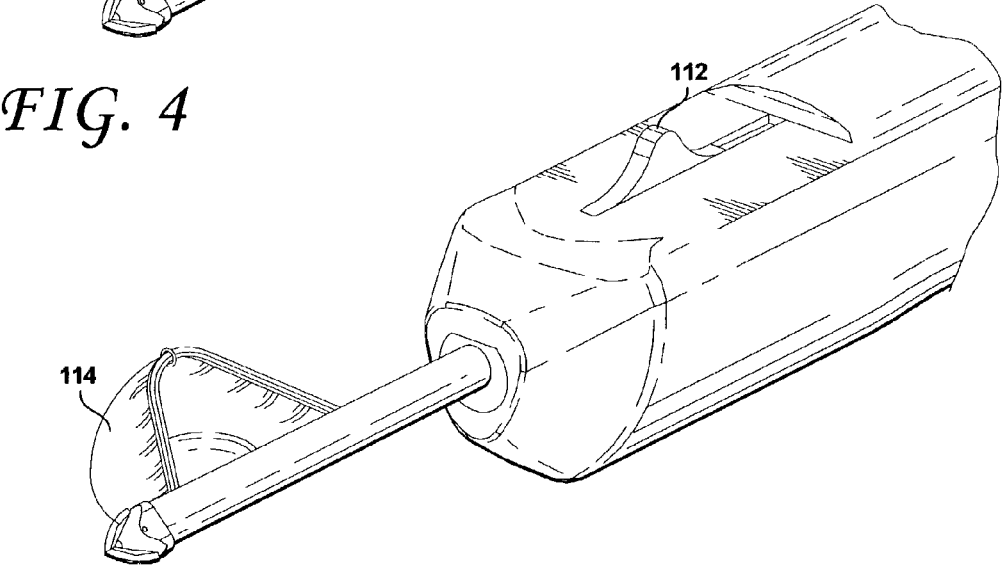
FIG. 5 shows the excisional device of FIG. 3, with the integrated cut and collect assembly in a fully expanded position.

FIGS. 3–5 collectively show the operation of integrated cut and collect assembly of the present excisional device. As shown in FIG. 3, the actuator 112 is in its proximal most position and the integrated cut and collect assembly 108 mechanically coupled thereto is in the substantially retracted position wherein both the cutting and collecting portions thereof are at least partially retracted within through 120 defined within the shaft 104. The flexible membrane 114 of the collecting portion may initially be folded, (at least partially) stowed in the trough 120 defined within the shaft 104, or simply loose. As the membrane 114 is preferably thin, smooth and flexible, it does not significantly hamper the insertion of the instrument as it penetrates the tissue mass. As shown in FIG. 4, sliding the actuator 112 in the distal direction causes the integrated cut and collect assembly 108 to expand in the direction shown by arrow 110. This expansion causes the cutting portion of the assembly 108 to bow radially out from the shaft 104 and the deployment of the flexible membrane 114 of the collecting portion. As the flexible membrane 114 is attached both to the outer surface of the shaft 104 and to the integrated cut and collect assembly 108, expansion of the integrated cut and collect assembly 108 opens the mouth of the bag shaped flexible membrane 114 and retraction thereof (FIG. 3) closes the mouth thereof. FIG. 4 shows the device 100 in a configuration wherein the actuator 112 is engaged to its distal most position and the integrated cut and collect assembly 108 is fully expanded. By varying the position of the actuator 112, the physician may achieve a fine grained control over the deployment of the integrated cut and collect assembly 108 to suit even an irregularly-shaped and sized specimen or lesion to be cut, collected, isolated and retrieved.

The integrated cut and collect assembly 108, according to the present invention, may include one or more mechanically coupled ribbons or wires. For example, the device 100 may include a first ribbon 116 of the cutting portion and a second ribbon 118 to which the flexible membrane 114 is attached. Alternatively, the flexible membrane 114 may be attached to a trailing edge of the ribbon 116 of the cutting portion of the integrated cut and collect assembly 108. In such an embodiment, the integrated cut and collect assembly 108 does not include separate but mechanically coupled cutting and collecting portions, but instead includes only a single ribbon 116 or other (RF) cutting element to which the flexible membrane 114 is attached. Other methods and means of attaching the flexible membrane to the cutting portion are disclosed hereunder. Such methods and means may draw upon the physical mechanical structure of the cutting portion, the collecting portion, the ribbon 116 and/or 118 and the material of the flexible membrane 114.

Figure 6:
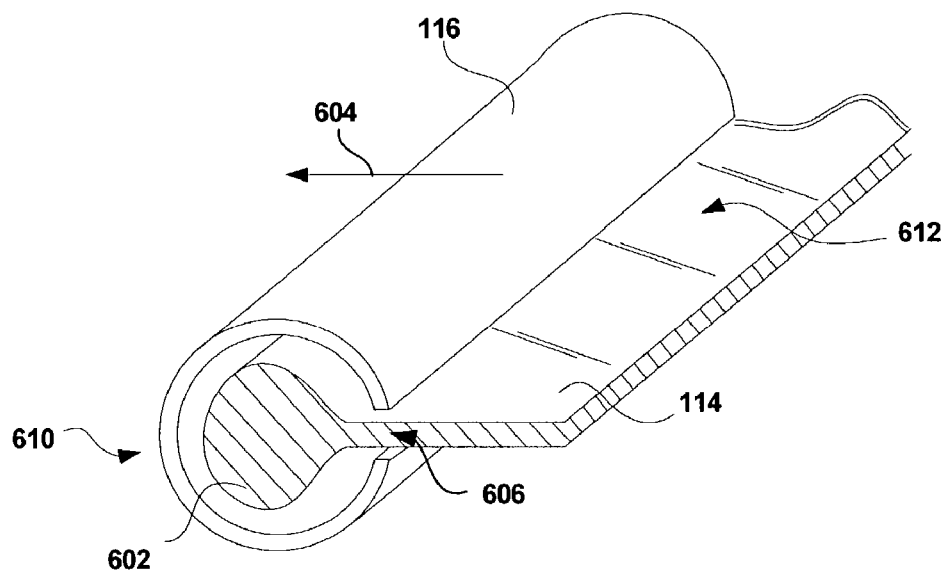
FIG. 6 shows an exemplary configuration of the integrated cut and collect assembly of the present invention, detailing the manner in which the collecting portion may be attached to the cutting portion of the integrated cut and collect assembly.

FIG. 6 shows an exemplary configuration of the integrated cut and collect assembly of the present invention, detailing one possible manner in which the collecting portion may be attached to the cutting portion of the integrated cut and collect assembly 108. As shown therein, the integrated cut and collect assembly 108 may include only a single ribbon 116. This single ribbon 116 forms the cutting portion of the assembly 108. According to this embodiment, the ribbon 116 may be configured as a flexible tube with a longitudinal slit 606 through which the flexible membrane 114 emerges. The flexible membrane 114, according to this embodiment, may include a locally thicker (bulbous, for example) portion 602 that is disposed within the interior lumen 608 defined by the tube-shaped ribbon 116. The slit 606 is oriented such that the flexible membrane 114 extends out of the trailing edge 612 of the ribbon 116. As the ribbon 116 is expanded and energized and the excisional device 100 rotated, the leading edge 610 of the ribbon 116 cuts through the tissue, while the flexible membrane 114 is deployed and trails behind, collecting, isolating and encapsulating the cut tissue. The ribbon 116 need not be shaped as a tube, but may assume any shape that efficiently cuts through the tissue and secures the flexible membrane 114 thereto. Moreover, the ribbon need not completely encircle the locally thicker portion 602 of the flexible membrane 114. The ribbon 116 may be advantageously formed of a conductive and resilient material such as stainless steel, titanium, tungsten or a shape-memory metal, such as a nickel titanium alloy sold under the name of Nitinol®, for example.

Figure 7:
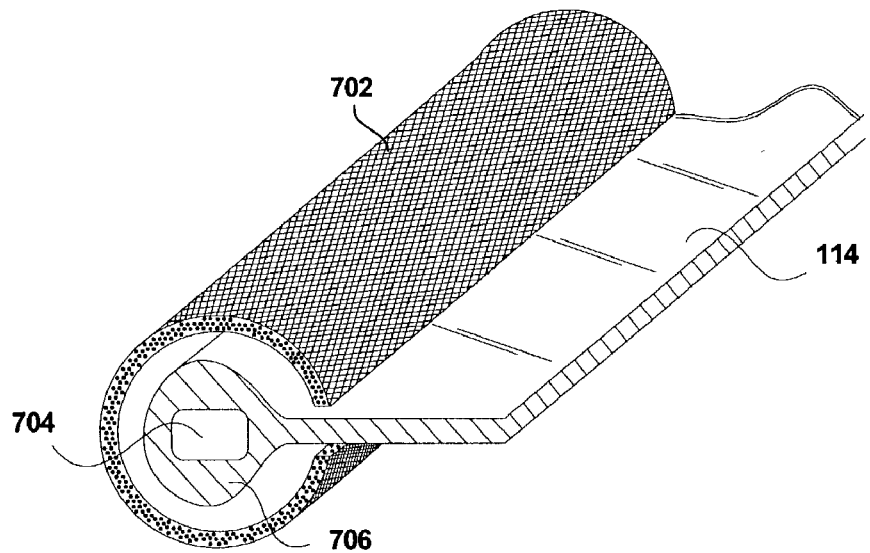
FIG. 7 shows another exemplary configuration of the integrated cut and collect assembly of the present invention.

As an alternative to the solid ribbon 116, the cutting portion of the integrated cut and collect assembly 108 may include or be formed of a plurality of wires or ribbons braided in such a manner as to form the tissue cutting ribbon, as shown at 702 in FIG. 7. To provide additional rigidity, a central reinforcing ribbon or mandrel 704 may be disposed within the interior lumen formed by the braided ribbon 702. As shown in FIG. 7, the locally thicker portion 706 of the flexible membrane 114 may be formed around the central reinforcing ribbon 704.

Figure 8A:
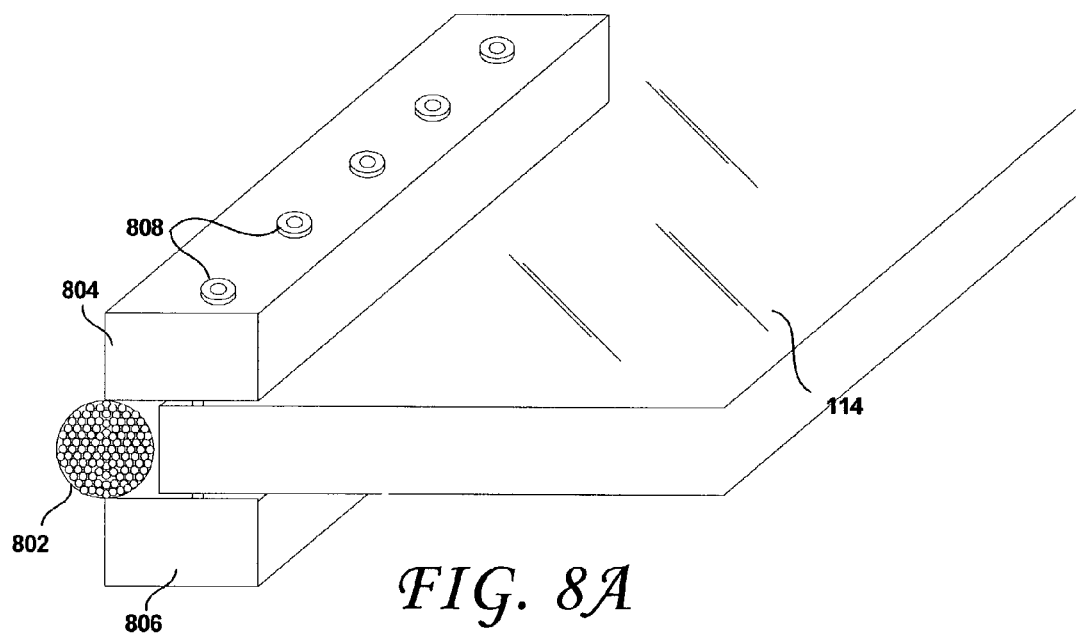
FIG. 8A shows yet another exemplary configuration of the integrated cut and collect assembly of the present invention, detailing the manner in which the collecting portion may be attached to the cutting portion of the integrated cut and collect assembly.

FIG. 8A shows another embodiment of the integrated cut and collect assembly 108. As shown, the flexible membrane 114 of the collecting portion may be sandwiched between two flexible plates 806, 808. Rivets, pins and/or welds 808 secure the two plates 804, 806 to one another with the flexible membrane 114 therebetween. The plates 804, 806 are preferably sufficiently flexible to selectively assume the retracted shape and the expanded and bowed shape of the integrated cut and collect assembly 108, as shown in FIGS. 3 and 5, respectively. The assembly of FIG. 8A may also include a solid or braided conductive (shown) ribbon or wire 802. The ribbon 802 may also be sandwiched between the two plates 804, 806 and held securely in place. In this case, the ribbon 802 defines the leading edge of the integrated cut and collect assembly 108 and the flexible membrane 114 the trailing edge thereof. The plates 804, 806 and the rivets, welds or pins 808 may be formed of a conductive material. In that case, when the ribbon 802 is energized with RF energy, the ribbon 802 and the plates 804, 806 are at a same voltage potential, which prevents or decreases the probability of arcing between the plates 804, 806 and the ribbon 802. Alternatively, only the wire or ribbon 802 may be formed of a conductive material and the plates 804, 806 and the rivets, welds or pins formed of an insulating material. In this case, only then wire or ribbon 802 is energized and cuts through the tissue.

Figure 8B:
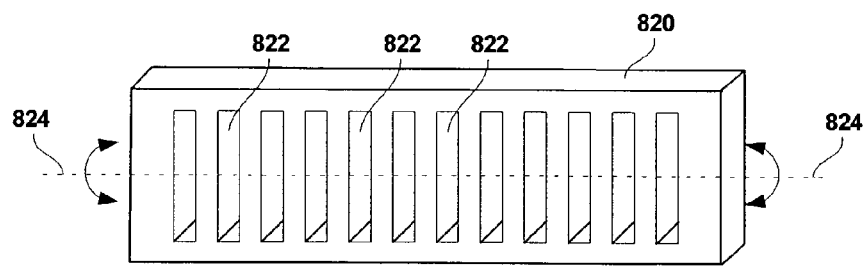
FIG. 8B shows still another exemplary configuration of the integrated cut and collect assembly of the present invention, detailing the manner in which the collecting portion may be attached to the cutting portion of the integrated cut and collect assembly.
Figure 8B:
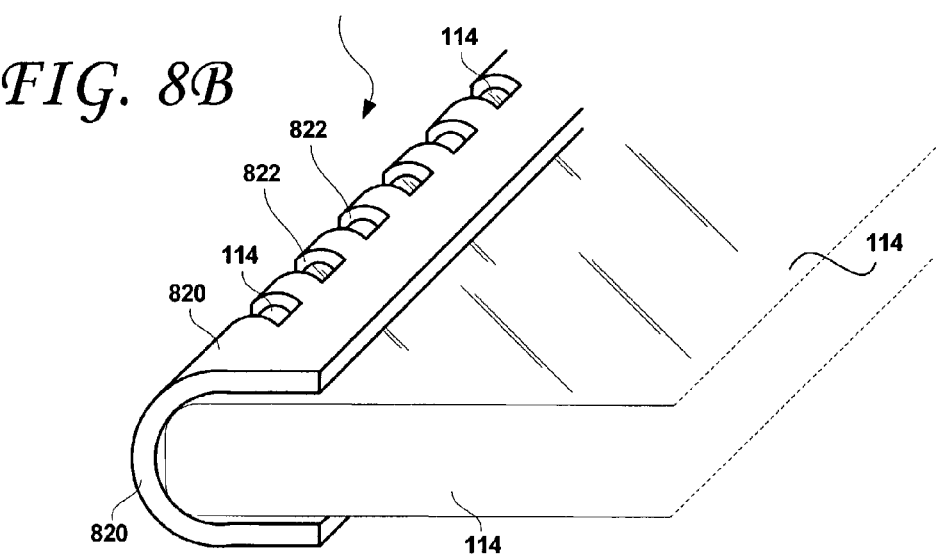

FIG. 8B shows yet another embodiment of the integrated cut and collect assembly 108, in which the collecting portion is directly attached to the cutting portion thereof. As shown therein, the cutting portion of the integrated cut and collect assembly 108 may include a windowed conductive plate 802. This conductive (metal, for example) plate 820 is preferably a thin plate in which openings 822 are defined. The thin plate 820, according to this embodiment, forms the cutting portion of the integrated cut and collect assembly 108. This cutting portion may be formed by bending the plate 820 along the longitudinal axis 824 to secure the flexible membrane 114 between the free edges thereof. The leading edge of the integrated cut and collect assembly 108, therefore, may be formed by the bent plate 820 whereas the trailing edge thereof includes the flexible membrane 114. The openings 822 in the plate 820 may facilitate the bending thereof, so as to allow the flexible membrane 114 to be securely attached thereto. Crimping of the free edges of the plate 820 and/or an adhesive may be used to secure the flexible membrane 114 to the plate 820. The windows or openings 822 may be defined within the plate 820 by stamping, through a photoetching technique or by cutting, as those of skill in this art will recognize.

Figure 8C:
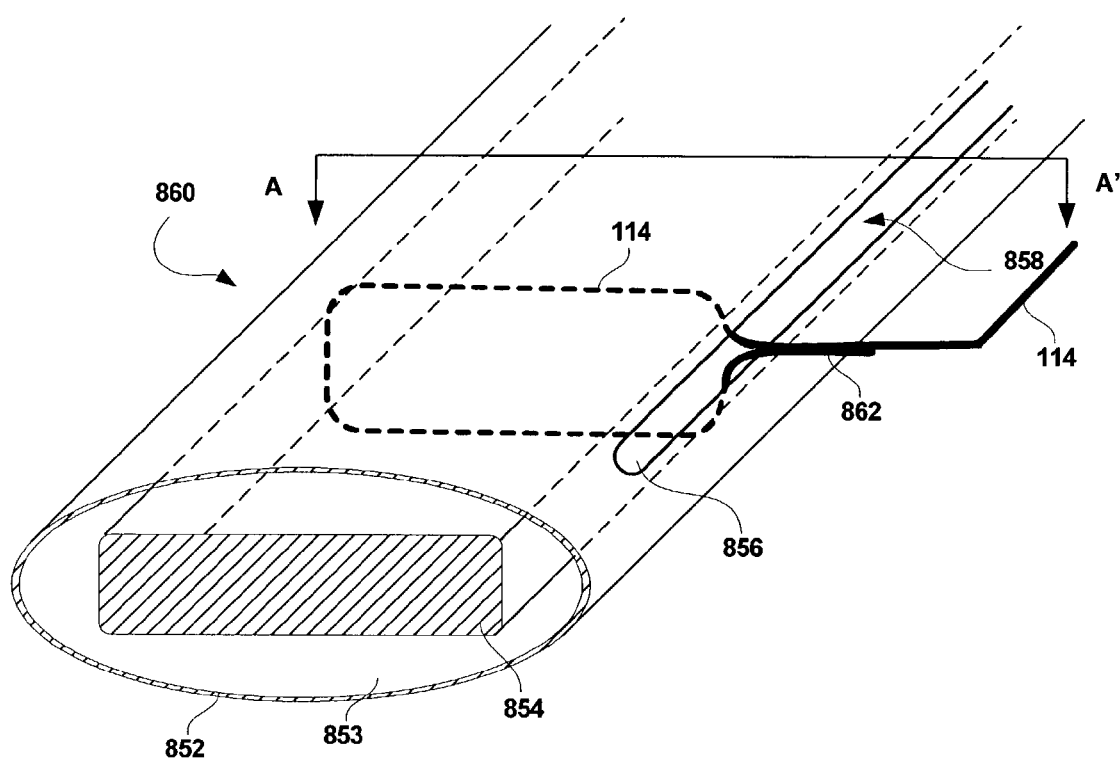
FIG. 8C shows a perspective and a cross sectional view of still another exemplary configuration of the integrated cut and collect assembly of the present invention.
Figure 8C:
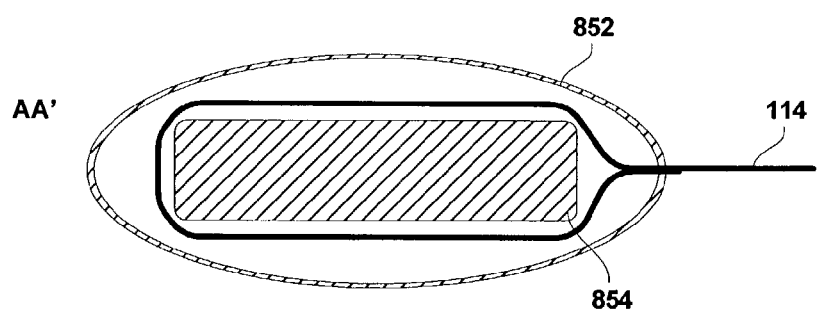

FIG. 8C shows a perspective and a cross sectional view of still another exemplary configuration of the integrated cut and collect assembly of the present invention. As shown therein, the cutting portion of the integrated cut and collect assembly 108 may be an elliptical cylinder that defines an interior lumen 853. The cutting portion 852 may be energized with RF energy, as discussed above. A mandrel 854 may be disposed within the cutting portion 852. A slot 856 is defined only within the trailing edge 858, and not within the leading (cutting) edge 860 of the cutting portion 851 of the integrated cut and collect assembly 108. The flexible membrane 114 loops around the mandrel and emerges from the cutting portion 852 from the slot 856. The flexible membrane 114 may be bonded at 862 after looping around the mandrel 854. Alternatively, the mandrel 854 may be inserted in a lumen formed by the flexible membrane 114. As with the other embodiments discussed relative to FIGS. 6, 7 and 8, the flexible membrane may also be attached to the outer surface of the shaft 104 by means of a tab, such as shown at reference numeral 220 in FIG. 2C, so as to allow the bag-shaped flexible membrane 114 to selectively open and close upon being acted upon by actuator 112.

Figure 8D:
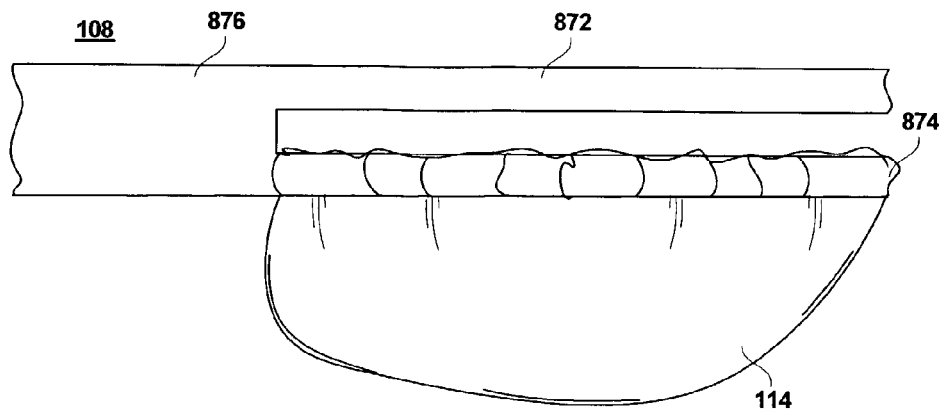
FIG. 8D shows yet another exemplary configuration of the integrated cut and collect assembly of the present invention, detailing the manner in which the collecting portion may be attached to the cutting portion of the integrated cut and collect assembly.

FIG. 8D shows yet another exemplary configuration of the integrated cut and collect assembly of the present invention, detailing the manner in which the collecting portion may be attached to the cutting portion of the integrated cut and collect assembly. As shown therein, the integrated cut and collect assembly 108 may be configured as a single ribbon 876 that defines a cutting portion 872 and a collecting portion 874. The single ribbon 876 may be split at least along the length of the trough 120 of the shaft 104. The distal ends of the cutting portion 872 and of the collecting portion 874 may be rejoined or may remain separate. The membrane 114 may define a lumen in which the free end of the collecting portion 874 may be introduced. Alternatively, the membrane 114 may be wrapped around the collecting portion 874 and secured thereto by means of an adhesive. The cutting portion 872 of the single ribbon 876 forms the leading edge of the integrated cut and collect assembly 108 as the device is rotated within the tissue and the specimen cut from the surrounding mass of tissue.

Figure 8E:
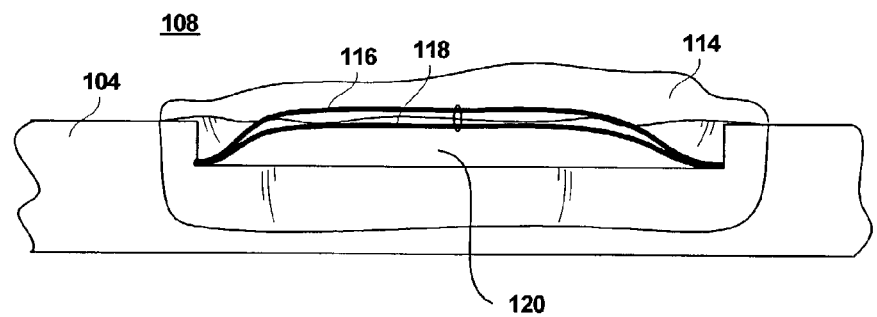
FIG. 8E shows a still further exemplary configuration of the integrated cut and collect assembly of the present invention.
Figure 8E:
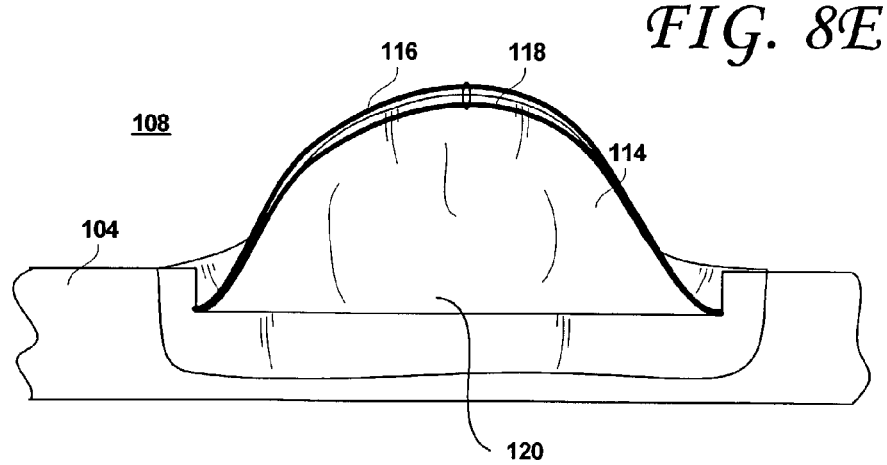

FIG. 8E shows another exemplary configuration of the integrated cut and collect assembly 108 of the present invention. The top figure of FIG. 8E shows the integrated cut and collect assembly 108 in the retracted position whereas the bottom figure shows the integrated cut and collect assembly 108 in the expanded position. As shown in the top figure, the membrane 114, when the integrated cut and collect assembly 108 is in the retracted position, is stretched across the trough 120. In this embodiment, the cutting portion of the integrated cut and collect assembly 108 may include a cutting ribbon 116 that emerges through the membrane 114 through a first slit therethrough and returns to the trough 120 through a second slit or opening defined therethrough. The cutting ribbon 116, therefore, is configured to be exposed to the tissue to be cut when the device is inserted within the patient and is located on a first external-facing surface of the membrane 114. The collecting portion of the integrated cut and collect assembly 108 may also include a collecting ribbon 118 that is located on a second surface of the membrane 114. The membrane may be attached to the shaft 104 such that when the integrated cut and collect assembly 108 is expanded in the radial direction relative to the shaft 104, the collecting ribbon 118 stretches the membrane 114 and causes the bag-shaped membrane 114 to define the mouth 222 (see FIG. 2C) of the collecting portion. After opening of the mouth or opening 222 by expansion of the integrated cut and collect assembly 108 and the stretching of the membrane 114 and after tissue has been collecting in the membrane 114, the integrated cut and collect assembly 108 may be retracted at least partially within the trough 120, causing the membrane 114 to return to the configuration shown in the top drawing of FIG. 8E. That is, the membrane 114 stretches back over the trough 120, thereby at least partially isolating the collected specimen from the surrounding tissue. In this embodiment, the collecting ribbon 118 may not be attached to the membrane 114. Indeed, the collecting ribbon 118 may only act upon the membrane 114 to stretch the membrane 114 open by pushing on it in the radial direction. When the specimen has been collected and the integrated cut and collect assembly integrated cutting and collecting assembly 108 retracted at least partially within the trough 120, the resilient nature of the membrane 114 causes the membrane to stretch back over the trough 120.

The foregoing has detailed a number of exemplary embodiments of the integrated cut and collect assembly 108. Those of skill in the art, however, may devise other alternative configurations and structures to integrate the cutting and collecting functions of reference numeral 108 into a single, mechanically coupled assembly that is actuable by a single actuator, such as shown at 112. All such alternative configurations, however, are deemed to fall within the purview of the present invention.

Figure 9:
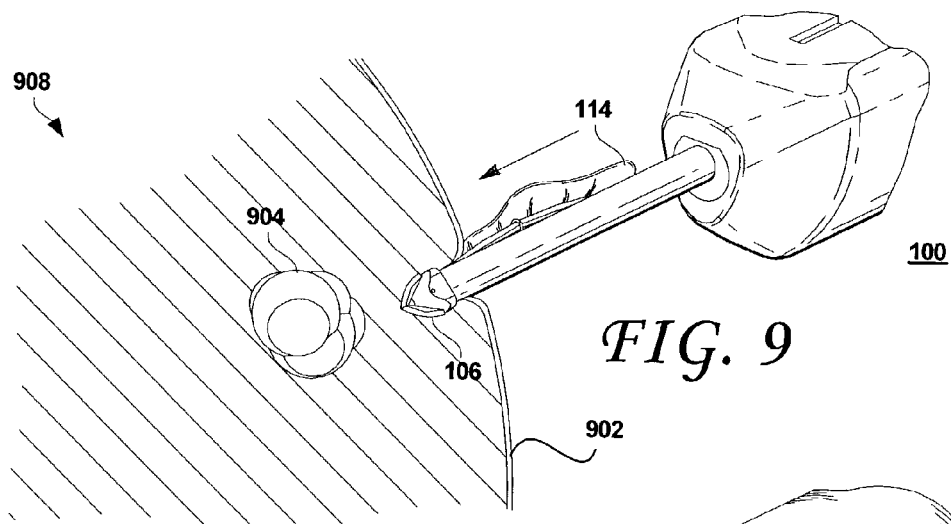
FIG. 9 illustrates aspects of the present method for cutting and collecting a tissue specimen from a mass of tissue, according to an embodiment of the present invention.
Figure 10:
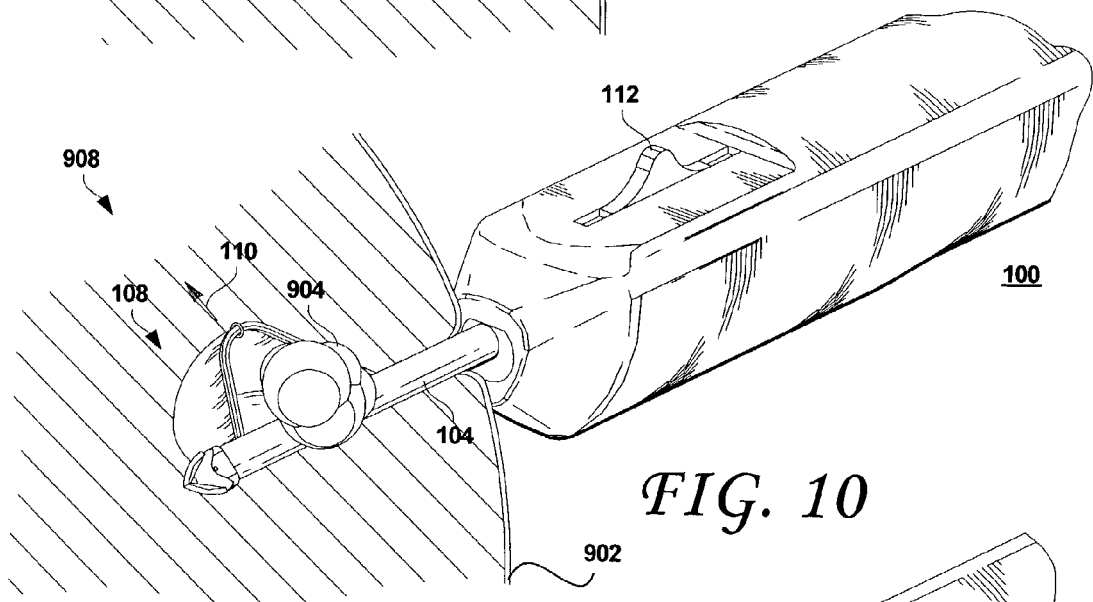
FIG. 10 illustrates further aspects of the present method for cutting and collecting a tissue specimen from a mass of tissue, according to an embodiment of the present invention.
Figure 11:
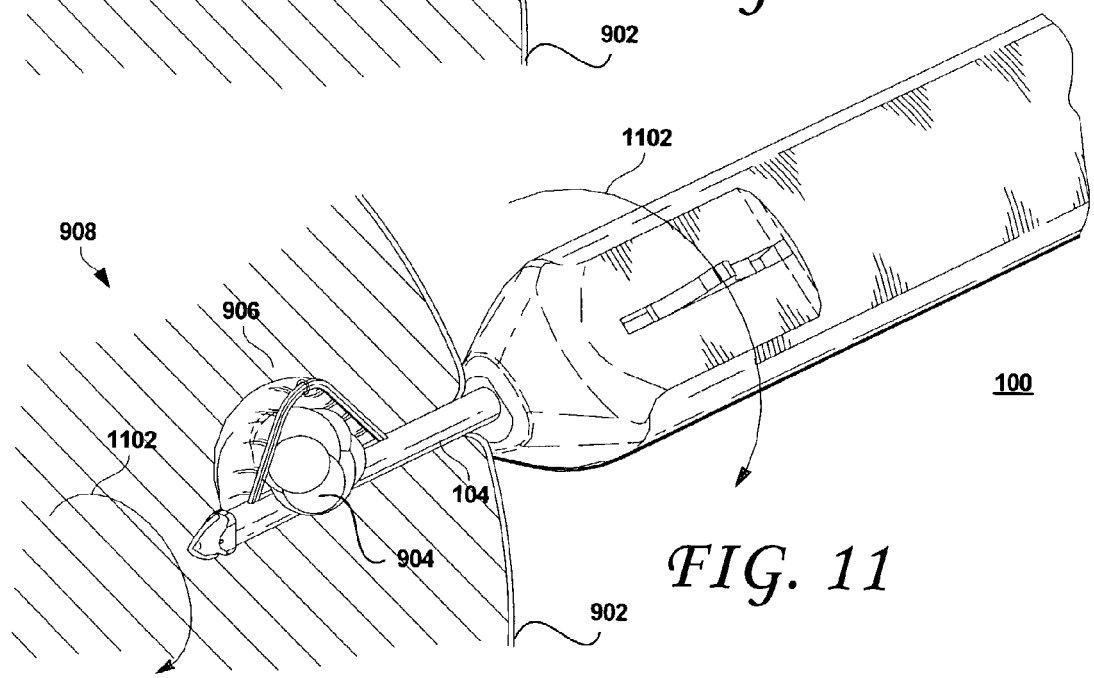
FIG. 11 illustrates still further aspects of the present method for cutting and collecting a tissue specimen from a mass of tissue, according to an embodiment of the present invention.
Figure 12:
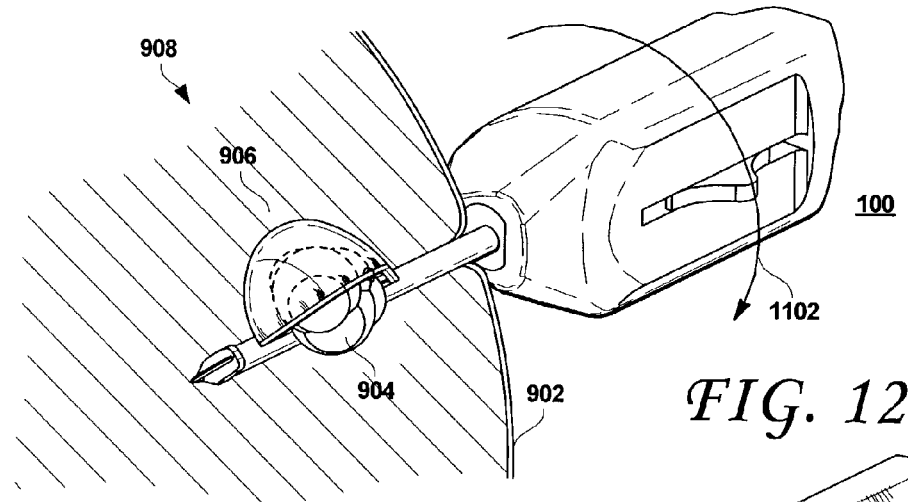
FIG. 12 illustrates further aspects of the present method for cutting and collecting a tissue specimen from a mass of tissue, according to an embodiment of the present invention.
Figure 13:
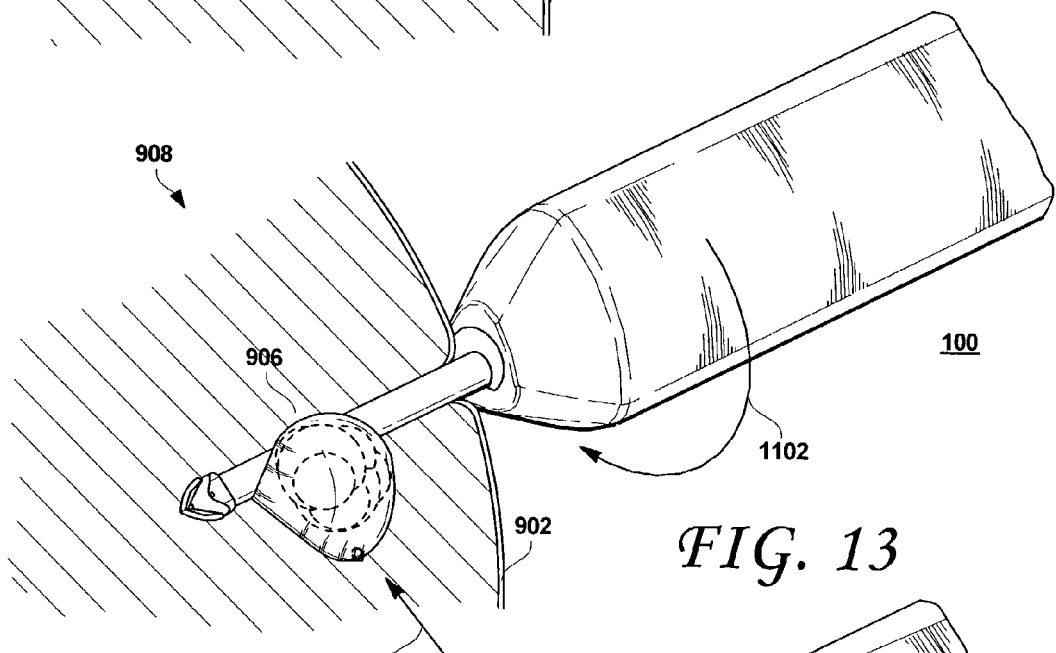
FIG. 13 illustrates further aspects of the present method for cutting and collecting a tissue specimen from a mass of tissue, according to an embodiment of the present invention.
Figure 14:
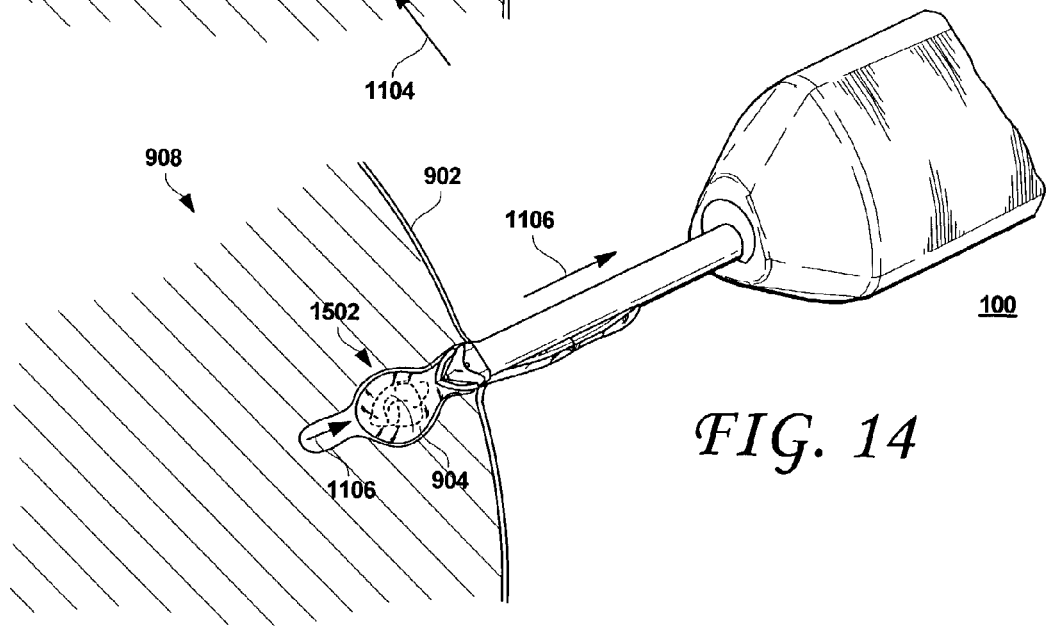
FIG. 14 illustrates further aspects of the present method for cutting and collecting a tissue specimen from a mass of tissue, according to an embodiment of the present invention in which the collected and isolated (encapsulated) tissue specimen trails the distal tip of the excisional device as it is retracted from the tissue.
Figure 15:
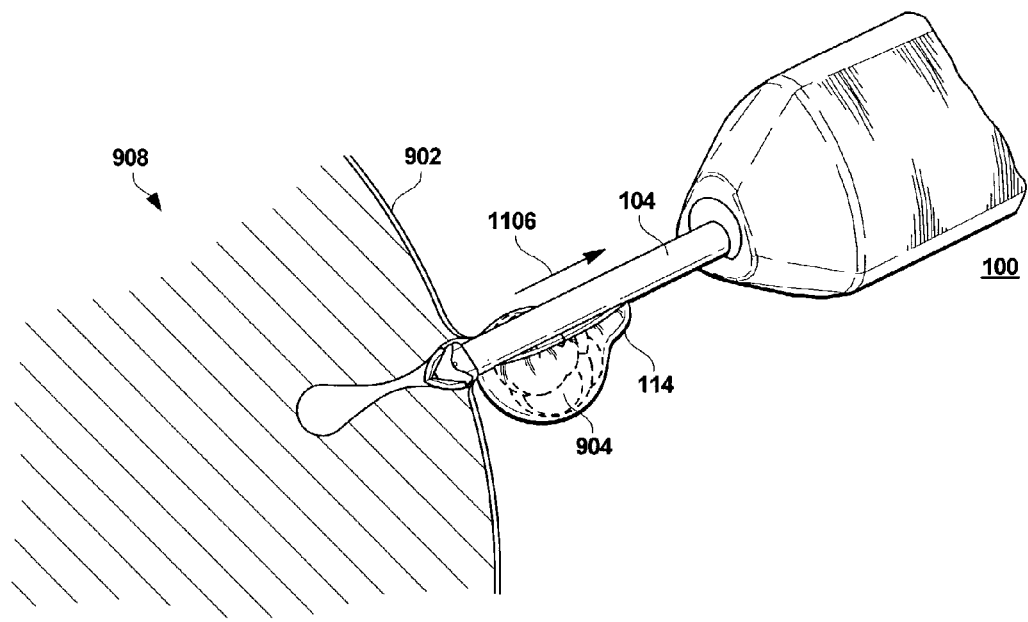
FIG. 15 illustrates further aspects of the present method for cutting and collecting a tissue specimen from a mass of tissue, according to another embodiment of the present invention in which the collected and isolated tissue specimen trails the distal end of the excisional device as it is retracted from the tissue.

FIGS. 9–16 show aspects of the present method for isolating a tissue specimen from surrounding tissue, according to embodiments of the present invention. As shown in FIG. 9, the excisional device 100 according to an embodiment of the present invention may be inserted through the skin 902 (or through the outermost tissue surface of the mass or organ from which the specimen is to be collected), either by making a prior incision therein or by allowing the distal tip 106 of the device 100 to make the initial cut. The distal tip 106 may be energized with RF energy during the insertion of the device 100 into the mass of tissue 908, but need not be. Satisfactory results are obtained by equipping the distal tip 106 with sharp blades and a conical shape, without the need for an RF energized tip. The integrated cut and collect assembly 108 should be initially in the retracted position, to enable it to readily penetrate the mass of tissue and advance to the target area (in this exemplary case, lesion 904) with the smallest possible profile. The shaft 104 may then be advanced (either through manual physician control or by means of a stereotactic setup) to a position wherein the integrated cut and collect assembly 108 is adjacent the target 904 and the target is approximately positioned in the middle of the integrated cut and collect assembly 108. As shown in FIG. 10, when the integrated cut and collect assembly 108 of the device 100 is positioned adjacent the target lesion 904, the integrated cut and collect assembly 108 may be expanded in the direction indicated by 110 by acting upon the actuator 112, after having fully energized the integrated cut and collect assembly 108 with RF energy, preferably while the integrated cut and collect assembly 108 is at least partially retracted within the trough 120. The integrated cut and collect assembly 108 may be expanded to up to its maximum expansion or to a selectable degree of expansion, advantageously under real time ultrasonic guidance and/or under another imaging modality. As shown at FIG. 11, the present excisional device 100 may then be rotated in the direction indicated by arrow 1102, while the integrated cut and collect assembly 108 remains energized with RF energy. In this manner, the leading edge of the RF-energized integrated cut and collect assembly 108 cuts through the tissue. Preferably the integrated cut and collect assembly 108 is expanded to a sufficient degree so as to cut a margin of healthy tissue around the target lesion 904, so as to decrease the probability of seeding abnormal cells (e.g., cancerous or pre-cancerous) into and around the excision site and the retraction path. As shown in FIG. 11, as the energized integrated cut and collect assembly 108 is rotated, it cuts around the lesion 904. As the trailing edge of the integrated cut and collect assembly 108 has deployed the collecting portion thereof, the cut lesion or specimen 904 is collected in the open bag formed by the trailing and close ended flexible membrane 114. As shown in FIGS. 12 and 13, the rotation 1102 of the device 100 may be continued as needed (preferably under ultrasonic guidance) until the specimen 904 has been at least partially severed from the surrounding tissue 906. At this point, the specimen 904 has been at least partially collected within the bag-shaped flexible membrane 114 of the collecting portion of the integrated cut and collect assembly 108. As shown at FIG. 14, to fully sever the specimen 904 from the surrounding tissue 906, the integrated cut and collect assembly 108, while still RF energized, may be retracted by acting proximally upon the actuator 112, thus causing the integrated cut and collect assembly 108 to move in the direction 1104 to capture and encapsulate the specimen 904 within the flexible membrane 114. As the bag-shaped flexible membrane is now closed, the cut and collected specimen is effectively isolated and encapsulated (or substantially isolated and encapsulated) from the surrounding tissue 906. Indeed, the cut and collected specimen 904 is now separated from the surrounding tissue by a layer of the flexible membrane 114. The RF to the integrated cut and collect assembly 108 may now be turned off.

As shown in FIG. 14, the cut, collected, encapsulated and isolated specimen 904 may then be recovered by retracting the device 100 from the mass of tissue 908 by moving the device 100 along the direction indicated at 1106. As shown in FIG. 14, the material of the flexible membrane 114 may be sufficiently elastic so as to allow the cut, collected and physically isolated specimen to stretch so as to at least partially trail the distal tip 106 as the device 100 is retracted along the insertion path through the mass of tissue 908, as shown at 1502 in FIG. 14. By configuring the integrated cut and collect assembly 108 so as to allow the specimen filled bag-shaped flexible membrane 114 to trail the distal tip 106, the initial incision into the skin and the diameter of the insertion and retraction path may be kept small, as neither the retraction path nor the incision need accommodate the full aggregate width of the shaft 104, the integrated cut and collect assembly 108 and the isolated specimen 904.

Figure 16:
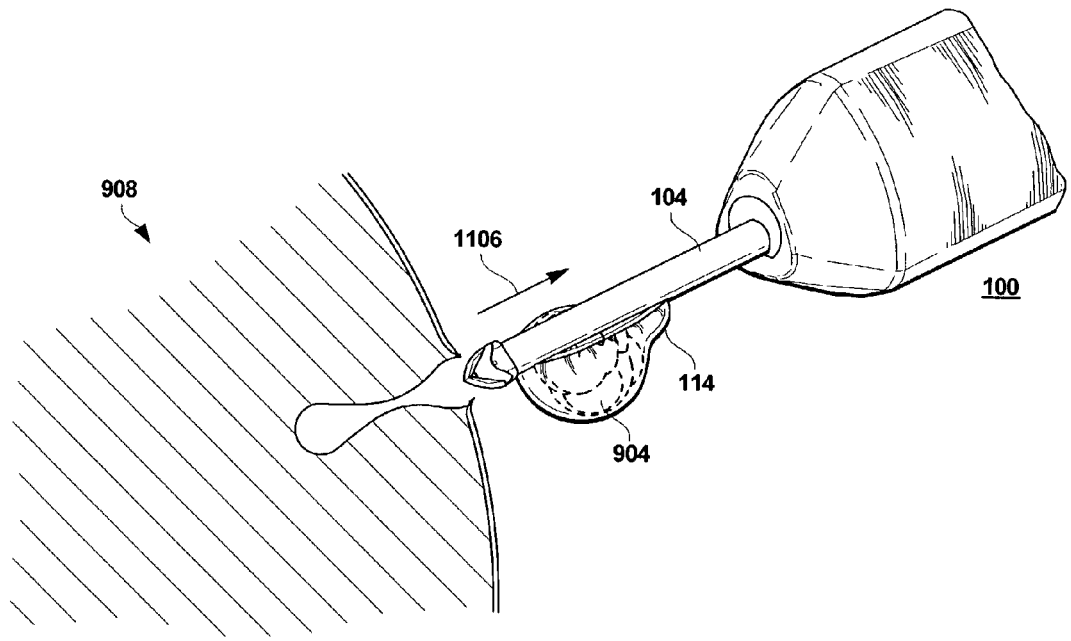
FIG. 16 illustrates still further aspects of the present method for cutting and collecting a tissue specimen from a mass of tissue, in which the excisional device containing the tissue specimen has been fully removed from the tissue mass from which the specimen was cut, collected and isolated.

As shown in FIG. 154, the specimen-filled flexible membrane of the collecting portion of the integrated cut and collect assembly 108 may be configured so that it does not substantially trail the distal tip, or only does so partially during retraction of the device 100 from the mass of tissue from which the specimen was cut. The material of the flexible membrane 114 (as detailed below) and the configuration thereof may be chosen so as to achieve the desired behavior during the collecting, isolating and retracting phases of the is present method. FIG. 16 shows a fully retracted device 100, containing a collected and isolated specimen 904 in which the tissue architecture has been maintained substantially intact. After full retraction of the device 100 from the mass of tissue, the incision within the skin 904 may be treated and closed according to standard surgical practices. During the excisional method detailed relative to FIGS. 9–16, the second lumen 206 (shown in FIG. 2A) within the shaft 104 may be used, for example, to evacuate smoke and/or bodily fluids (e.g., blood) from the excision site within the mass of tissue 908. Alternatively the second lumen 206 defined within the shaft 104 may be used to deliver a pharmaceutical agent to the excisional site, such as, for example, an anesthetic, an analgesic and/or some other agent. The inflatable balloon 208 shown in FIG. 2A may be may be inflated with, for example, a gas (air or carbon dioxide, for example) or a fluid (such as saline, for example). The balloon 208 may assist in stabilizing the present excisional device within the tissue mass after insertion therein and/or to provide some degree of hemostasis during the excisional procedure.

The flexible membrane 114 is preferably non-conductive and stable at high temperatures. For example, the material used in the flexible membrane should be RF resistant (i.e., have the ability to withstand the temperatures generated by the RF-energized cutting portion of the integrated cut and collect assembly integrated cutting and collecting assembly 108). The flexible membrane 11, therefore, should be stable (i.e., acceptably maintains its structural integrity and does not unacceptably melt, deform, burn or lose cohesion, tensile or shear strength) at temperatures at which the energized cutting portion operates. According to one embodiment of the present invention, the flexible membrane includes a non-main chain carbon based polymeric material, such as a silicone elastomer (such as polydimethylsiloxane, for example) or a silicone-containing elastomer. For example, the flexible membrane 114 of the collecting portion of the integrated cut and collect assembly 108 may include one or more of the following materials: an organic, inorganic or organic-inorganic polymer such as a silicone elastomer or a silicone-containing elastomer, a teraphthalate, a tetrafluoroethylene, a polytetrafluoroethylene, a polyimid, a polyester, a polyolephin, Kevlar® and/or M5®, for example. The flexible membrane 114 may have a laminar structure that includes one or more reinforcing layers. Such reinforcing layers may include, for example, any of the above-listed materials and/or polyester, polyurethane or polyimid, for example. For example, the flexible membrane 114 may include NuSil 10-6640, a material manufactured by NuSil Technology of Carpinteria, Calif. The thickness of the flexible membrane may be freely chosen according to the desired characteristics of the collecting portion of the integrated cut and collect assembly 108. For example, the flexible membrane 114 may be between about 0.0005 and about 0.1 inches. For example, the flexible membrane 114 may be chosen to have a thickness between about 0.0007 and 0.005 inches. For example, the flexible membrane 114 may be selected to have a thickness of between 0.001 and 0.015 inches.

When an adhesive is used to secure the flexible membrane to other structures of the device or the integrated cut and collect assembly 108, a strong, biologically inert and safe adhesive may be used. Advantageously, a silicone containing or based adhesive or a cyanoacrylate containing or based adhesive may be used with good results.

In an aspect of the present invention, and as can be appreciated from the description and drawings provided herein, the devices and methods of the present invention may provide for retraction of tissue away from the ribbon 116 which cuts tissue. For example, FIGS. 1B, 1C, 2B, 2C, 2E and 2F show the ribbon 118 holding the membrane 114 partially or completely covering part of the ribbon 116 such as a radially inner side RI. The ribbon 118 and/or a tissue collection assembly 115 prevents tissue from contacting part of the radially inner RI side of the cutting ribbon 116 and, in particular, the trailing edge TE or trailing side TS of the ribbon 116 opposite the cutting side CS. This feature can provide advantages when starting or re-starting the RF cutting ribbon 116 when the ribbon 116 is already within tissue. By reducing the overall surface area of the RF cutting ribbon 116 that is exposed to tissue, the current density along other parts of the ribbon 116 may be sufficient to start the device using a conventional RF generator, optionally with an increased voltage applied to the ribbon 116. This cannot be said of many prior art bowed RF cutting elements that provide cutting blades or ribbons exposed on both the radially inner and outer sides. Other means of reducing the surface area of the RF cutting ribbon 116 that is exposed to tissue are disclosed in commonly assigned and copending U.S. application Ser. No. 09/732,848 filed on Dec. 7, 2000, which is incorporated herewith in its entirety.

In another method and device of the present invention, the device may have a thickened portion 117 that trails the cutting side CS of the ribbon 116. The thickened portion 117 retracts tissue away from the ribbon 116 providing the advantage described above. The thickened portion 117 may be at least two or even three times larger than the thickness of the ribbon 116. The thickened portion 117 may be recessed from the cutting side CS by a distance of less than 0.25 inch or even less than 0.10 inch (FIG. 2E) or about 0.015 inch although any configuration may be used. Referring to FIG. 1B, the thickened portion is provided by the ribbon 118 and membrane 114 which cover the radially inner side RI of the ribbon 116 through which energy to cut tissue is transmitted. The thickened portion 117 may also simply be provided by the membrane 114 itself or another part of the tissue collection assembly 115. As the membrane is drawn over the tissue being collected, the collapsed membrane 114 can also retract tissue away from the ribbon 116.

Referring to FIG. 1C, the device may also provide for retraction of tissue away from the radially outer RO side of the ribbon 116. The device of FIG. 1C is the same as the device of FIG. 1B except that the member 124 has been replaced by an element 125 which extends radially outward from the ribbon 116. The element 125 is essentially a U-shaped sleeve of material having an opening to fit around the trailing side of the ribbon 116. The sleeve does not transmit RF energy to cut tissue and, in this sense, insulates the ribbon as well as providing retraction away from the cutting side CS. Of course, the element 125 providing retraction of tissue may also transmit RF to cut tissue without departing from various aspects of the invention. The element 125 may be retained by ribbon 116, ribbon 118, member 124, or the tissue collection assembly 115 such as the membrane 114. Finally, as can be readily appreciated, the ribbon 118 may be separately movable from the ribbon 116 with a separate actuator having similar structure as actuator for ribbon 116 thereby allowing the user to selectively cover parts of the ribbon 116. In still another aspect of the devices and methods of the present invention, the devices may reduce transmission of energy to cut tissue through parts of the cutting ribbon 116 to the tissue so that the current density is increased at other portions thereof to initiate RF cutting. The tissue retraction devices described above also provide a gap between the ribbon 116 and tissue which can help initiate RF cutting by providing an ionizing path between the tissue and ribbon. For example, the gap may be simply filled with air, argon, saline or another suitable gas or liquid.

Another way of preventing transmission of energy from parts of the ribbon 116 to the tissue is to coat the ribbon 116 with a coating 119 such as silicone, ceramic and PTFE. The coating 119 may be applied to any part of the ribbon 116. For example, the trailing side of the ribbon 116 may be coated to essentially coat half the ribbon 116. By coating the ribbon 116 in this manner, half of the cutting ribbon 116 remains exposed for transmitting cutting energy to the tissue. As used herein, the effective width shall mean the part of the ribbon that is exposed to tissue. By coating half the ribbon, for example, the effective width is half the width of the ribbon 116. When partially covering, coating or retracting tissue away from the radially inner and/or radially outer side, one side may have an exposed part which is at least 20% larger, and even 35% larger, than an exposed part of the other side. Of course, the radially outer side may also be completely covered, coated or tissue may be retracted completely away from the radially inner side without departing from numerous aspects of the invention. For example, if the ribbon is recessed only a small amount, such as 0.015 inch, and covered by the membrane 114 the radially inner side will completely covered as shown in FIG. 2F. Finally, other ways of preventing transmission of RF energy to the tissue and/or retracting tissue away from the cutting element can be appreciated from commonly assigned and copending U.S. patent application Ser. No. 10/098,014 filed on Mar. 14, 2002 and commonly assigned and copending U.S. patent application Ser. No. 10/066,428 filed on Jan. 31, 2002, which are hereby incorporated by reference.

In a further aspect of the present invention, the cutting ribbon 116 has an exposed length which cuts tissue which may be 25, 40 or even 100 times larger than the ribbon 116 width or effective width and a length to thickness ratio twice as large. The relatively thin, elongate ribbon 116 maintains sufficient mechanical stability and integrity to sweep through many tissue types. A problem encountered by more robust ribbons known in some prior art is that these ribbons may have difficulty initiating an RF arc within tissue since the ribbons have such large surface areas in contact with tissue. For a given applied voltage, the large surface area reduces the likelihood that the current density will be sufficient to initiate RF cutting using common RF generators. The relatively narrow ribbons of the present invention minimize this problem. Although the ribbon 116 is relatively small, the present invention may be used to remove relatively large tissue masses. In a preferred embodiment, for example, the ribbon 116 has a length of about 1.9 inch, a width of about 0.027 inch and a thickness of about 0.012 inch, which provides a length to width ratio of about 70 to 1 and a length to thickness ratio of over 158 to 1. Of course, the cutting element (ribbon 116) may be configured in a number of different sizes without departing from the invention. When using the device to extract relatively large intact portions of tissue from the breast, the cutting element preferably has a tissue-exposed length of about 1.5 to 5.5 inch. The cutting element is preferably made of stainless steel such as 304 stainless steel, but may, of course, be made of or include any other suitable material such as tungsten, titanium or another stainless steel. The device preferably has only one cutting element mounted to the shaft, or stated another way, has one cutting surface or cutting edge, although more cutting elements or ribbons may be used with some aspects of the present invention.

While the foregoing detailed description has described preferred embodiments of the present invention, it is to be understood that the above description is illustrative only and not limiting of the disclosed invention. For example, the shape of the flexible membrane 114 may differ from that described and depicted herein, as may the structure of the integrated cut and collect assembly 108. Those of skill in this art will recognize other alternative embodiments and all such embodiments are deemed to fall within the scope of the present invention. Thus, the present invention should be limited only by the claims as set forth below.

What is claimed is:

1. A method of cutting breast tissue using RF energy, comprising the steps of:
    providing a device having an elongate RF cutting element and a tissue collection element, the elongate RF cutting element having a cutting side, the elongate cutting element including a portion of non RF-transmissive material disposed away from the cutting side, the portion of non RF-transmissive material being separate from and forming no part of the tissue collection element, the RF cutting element being movable between a bowed position and a straightened position;
    introducing the device into a patient's breast;
    activating the RF cutting element;
    moving the RF cutting element to the bowed position;
    retracting tissue away from the cutting side of the RF cutting element while the RF element is in the bowed position by pushing the tissue over the portion of non RF-transmissive material; and
    rotating the device to cut a portion of breast tissue with the cutting side of the RF cutting element.

2. The method of claim 1, wherein:
    the providing step is carried out with the portion of non RF-transmissive material trailing the cutting side.

3. The method of claim 2, wherein:
    the providing step is carried out with the portion of non RF-transmissive material being at least two times larger than a cutting element thickness.

4. The method of claim 2, wherein:
    the providing step is carried out with the portion of non RF-transmissive material being at least three times larger than a cutting element thickness.

5. The method of claim 2, wherein:
    the providing step is carried out with the portion of non RF-transmissive material being spaced from the cutting side by a distance of less than 0.25 inch.

6. The method of claim 2, wherein:
    the retracting step is carried out with the tissue collection element trailing the cutting element.

7. The method of claim 2, wherein:
    the retracting step is carried out with the thickened portion retracting tissue away from a radially inner surface of the cutting element when the cutting element is in the bowed position.

8. The method of claim 7, wherein:

the providing step is carried out with the portion at non RF-transmissive material retracting tissue away from a radially outer surface of the RF cutting element.

9. The method of claim 2, wherein:

the providing step is carried out with the portion of non RF-transmissive material retracting tissue away from a radially outer surface of the RF cutting element.

10. The method of claim 2, wherein:

the retracting step is carried out with a side of the cutting element opposite the cutting side being electrically insulated so that RF energy is not delivered to the tissue from the side of the cutting element opposite the cutting side.

11. A device for cutting breast tissue using RF energy, comprising:

a shaft;

an elongate RF cutting element coupled to the shaft, the elongate RF cutting element having a cutting side, the elongate cutting element being movable between a bowed position and a straightened position;

a tissue collection element coupled to the shaft, the tissue collection element being configured to collect tissue cut by the cutting element, and a tissue retractor which is also movable between a bowed position and straightened position independently of the cutting element, the tissue retractor having a thickened portion positioned to retract tissue away from the cutting element when the cutting element and tissue retractor are in the bowed positions, the tissue retractor being separate from and forming no part of the tissue collection element.

12. The device of claim 11, wherein:

the shaft has a longitudinal axis, wherein rotation of the shaft about the longitudinal axis moves the cutting element through the tissue.

13. The device of claim 11, wherein:

the tissue retractor is positioned adjacent a radially inner side of the cutting element when the tissue retractor and cutting element are in the bowed positions.

14. The device of claim 11, wherein:

the tissue retractor includes a membrane, whereby the membrane provides the thickened portion when in a collapsed configuration.

15. The device of claim 11, wherein:

the thickened portion is at least two times larger than a cutting element thickness.

16. The device of claim 11, wherein:

the thickened portion is at least three times larger than a cutting element thickness.

17. The device of claim 11, wherein:

the thickened portion is spaced from the cutting side by a distance of less than 0.25 inch.

18. The device of claim 11, wherein:

the thickened portion is formed at least in part by an electrical insulation which covers part of the cutting element.

19. The device of claim 11, wherein:

a side of the RF cutting element opposite the cutting side is insulated so that RF energy is not delivered to the tissue from the side opposite the cutting side.

20. The device of claim 11, wherein:

the thickened portion retracts tissue away from a radially inner surface of the cutting element when the cutting element is in the bowed position.

21. The device of claim 11, wherein:

the thickened portion retracts tissue away from a radially outer surface of the cutting element when the cutting element is in the bowed position.

22. The device of claim 11, wherein:

the thickened portion retracts tissue away from both a radially inner surface and a radially outer surface of the cutting element when the cutting element is in the bowed position.

* * * * *

UNITED STATES PATENT AND TRADEMARK OFFICE
CERTIFICATE OF CORRECTION

| | | |
|---|---|---|
| PATENT NO. | : 7,044,956 B2 | Page 1 of 1 |
| APPLICATION NO. | : 10/272452 | |
| DATED | : May 16, 2006 | |
| INVENTOR(S) | : James W. Vetter et al. | |

It is certified that error appears in the above-identified patent and that said Letters Patent is hereby corrected as shown below:

Column 29, line 2, replace [at] with -- of --.

Signed and Sealed this

Eleventh Day of July, 2006

JON W. DUDAS
*Director of the United States Patent and Trademark Office*